United States Patent
Kondou

(10) Patent No.: US 8,741,229 B2
(45) Date of Patent: Jun. 3, 2014

(54) SAMPLE ANALYZER, REAGENT INFORMATION DISPLAYING METHOD AND COMPUTER PROGRAM PRODUCT

(75) Inventor: Keitarou Kondou, Kobe (JP)

(73) Assignee: Sysmex Corporation, Kobe (JP)

( * ) Notice: Subject to any disclaimer, the term of this patent is extended or adjusted under 35 U.S.C. 154(b) by 806 days.

(21) Appl. No.: 12/607,720

(22) Filed: Oct. 28, 2009

(65) Prior Publication Data

US 2010/0115463 A1     May 6, 2010

(30) Foreign Application Priority Data

Oct. 31, 2008 (JP) ................................. 2008-282351

(51) Int. Cl.
*G01N 31/00* (2006.01)
(52) U.S. Cl.
USPC .............. 422/400; 422/62; 422/68.1; 436/43; 436/50; 700/266
(58) Field of Classification Search
None
See application file for complete search history.

(56) References Cited

U.S. PATENT DOCUMENTS

| | | | |
|---|---|---|---|
| 2005/0175506 A1* | 8/2005 | Matsubara et al. | 422/68.1 |
| 2005/0246288 A1 | 11/2005 | Kimura et al. | |
| 2006/0247866 A1* | 11/2006 | Mishima et al. | 702/19 |
| 2008/0014118 A1* | 1/2008 | Kitagawa et al. | 422/64 |
| 2008/0063570 A1 | 3/2008 | Fujino et al. | |
| 2008/0241937 A1 | 10/2008 | Wakamiya et al. | |

FOREIGN PATENT DOCUMENTS

| | | |
|---|---|---|
| JP | 10/040305 | 2/1998 |
| JP | 2003-116542 A | 4/2003 |
| JP | 2005/108115 | 4/2005 |
| JP | 2005/316634 | 11/2005 |
| JP | 2008/70115 A | 3/2008 |
| JP | 2008/249600 A | 10/2008 |

* cited by examiner

*Primary Examiner* — Sam P Siefke
(74) *Attorney, Agent, or Firm* — Sughrue Mion, PLLC

(57) ABSTRACT

The present invention is to present a sample analyzer, comprising: a reagent holder for holding a first and a second reagents; a display; a display controller for controlling the display so as to display a display screen including a first information displaying region for displaying one of a plurality of reagent information regarding the first reagent and a second information displaying region for displaying one of a plurality of reagent information regarding the second reagent; and a display switch receiver for receiving a display switch instruction of reagent information displayed in each of the first and second information displaying regions, wherein the display controller switches a first reagent information displayed in the first information displaying region to a second reagent information and switches a third reagent information displayed in the second information displaying region to a fourth reagent information, when the display switch receiver has received the display switch instruction.

19 Claims, 30 Drawing Sheets

SAMPLE ANALYZER, REAGENT INFORMATION DISPLAYING METHOD AND COMPUTER PROGRAM PRODUCT

FIELD OF THE INVENTION

The present invention relates to a sample analyzer, a method for displaying reagent information in a sample analyzer, and a computer program product, and in particular, to a sample analyzer for measuring a measurement sample prepared from a sample and a reagent, a method for displaying reagent information in a sample analyzer, and a computer program product.

BACKGROUND

Conventionally, for example, US Patent Publication No. 2008/063570 discloses a sample analyzer for measuring a measurement sample prepared from a sample and a reagent.

The sample analyzer disclosed in US Patent Publication No. 2008/063570 is configured to analyze the sample using plural kinds of reagents, and includes a reagent placing section for placing a plurality of reagents. The sample analyzer disclosed in US Patent Publication No. 2008/063570 is also configured to display on a display a reagent management screen including a reagent placing display region showing the arrangement state of the reagent in the reagent placing section and a detailed information displaying region for displaying the detailed information of the reagent. A reagent mark corresponding to each reagent is displayed in a specifiable manner in the reagent placing display region, and the detailed information (e.g., remaining amount of reagent, expiration date, and the like) of the reagent corresponding to the specified reagent mark is displayed in the detailed information displaying region.

The user of the sample analyzer desires to check not only the detailed information of a specified reagent but also the detailed information of a plurality of reagents placed in the reagent placing section on one display screen in order to easily grasp the detailed information of a plurality of reagents placed in the reagent placing section.

However, even if the detailed information of a plurality of reagents placed in the reagent placing section is attempted to be displayed on one display screen in order to respond to such demand, it is difficult to display all kinds of reagent information of each reagent on one display screen since the display area is limited in the display screen. Furthermore, the detailed information of one reagent includes plural kinds of reagent information such as the remaining amount and the expiration date of the reagent, but the information the user desires to check is often only part of the plural kinds of reagent information. Thus, if all kinds of reagent information are displayed for the plurality of reagents placed in the reagent placing section, the information other than the information required by the user are also displayed, which is excessive information to the user. In this case, the user has to search for the necessary information from the plural kinds of information. Therefore, it is difficult to grasp the necessary information.

SUMMARY

A first aspect of the present invention is a sample analyzer, comprising:
a reagent holder for holding a first reagent and a second reagent used for analysis of a sample;
a display;
a display controller for controlling the display so as to display a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information; and
a display switch receiver for receiving a display switch instruction of reagent information displayed in each of the first and second information displaying regions,
wherein the display controller switches the first reagent information displayed in the first information displaying region to the second reagent information and switches the third reagent information displayed in the second information displaying region to the fourth reagent information, when the display switch receiver has received the display switch instruction.

A second aspect of the present invention is a sample analyzer, comprising:
a reagent holder for holding a first reagent and a second reagent used for analysis of a sample;
a display; and
a control processing unit configured to perform operations comprising:
controlling the display so as to display a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information;
receiving a display switch instruction of reagent information displayed in each of the first and second information displaying regions; and
switching the first reagent information displayed in the first information displaying region to the second reagent information, and switching the third reagent information displayed in the second information displaying region to the fourth reagent information, when received the display switch instruction.

A third aspect of the present invention is a reagent information displaying method in a sample analyzer including a reagent holder for holding a first reagent and a second reagent used for analysis of a sample, and a display, comprising:
displaying, on the display, a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information;

receiving a display switch instruction of reagent information displayed in each of the first and second information displaying regions; and switching the first reagent information displayed in the first information displaying region to the second reagent information, and switching the third reagent information displayed in the second information displaying region to the fourth reagent information, when received the display switch instruction.

A fourth aspect of the present invention is a computer program product for enabling a computer to control a display device in a sample analyzer which comprises a reagent holder for holding a first reagent and a second reagent used for analysis of a sample, comprising:

a computer readable medium, and software instruction, on the computer readable medium, for enabling the computer to perform predetermined operations comprising:

controlling the display device so as to display a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information;

receiving a display switch instruction of reagent information displayed in each of the first and second information displaying regions; and switching the first reagent information displayed in the first information displaying region to the second reagent information, and switching the third reagent information displayed in the second information displaying region to the fourth reagent information, when received the display switch instruction.

DETAILED DESCRIPTION OF THE EMBODIMENT

The embodiments embodying the present invention will now be described based on the drawings.

First, with reference to FIGS. 1 to 21, the structure of a sample analyzer 1 according to one embodiment of the present invention will be described. The sample analyzer 1 according to one embodiment of the present invention is an apparatus for optically measuring and analyzing the amount or degree of activity of a specific substance related to coagulation and fibrolytic function of the blood, and uses blood plasma for the sample. In the sample analyzer 1 according to the present embodiment, the sample is optically measured using coagulation time method, synthetic substrate method, and immunoturbidimetric method. The coagulation time method used in the present embodiment is a measuring method of detecting the process the sample coagulates as change in transmitted light. The measurement items include PT (prothrombin time), APTT (activated partial thromboplastin time), Fbg (Fibrinogen content) or the like. The measurement item of the synthetic substrate method includes ATIII and the like, and the measurement item of the immunoturbidimetric method includes D dimer, FDP and the like.

Figure 1:
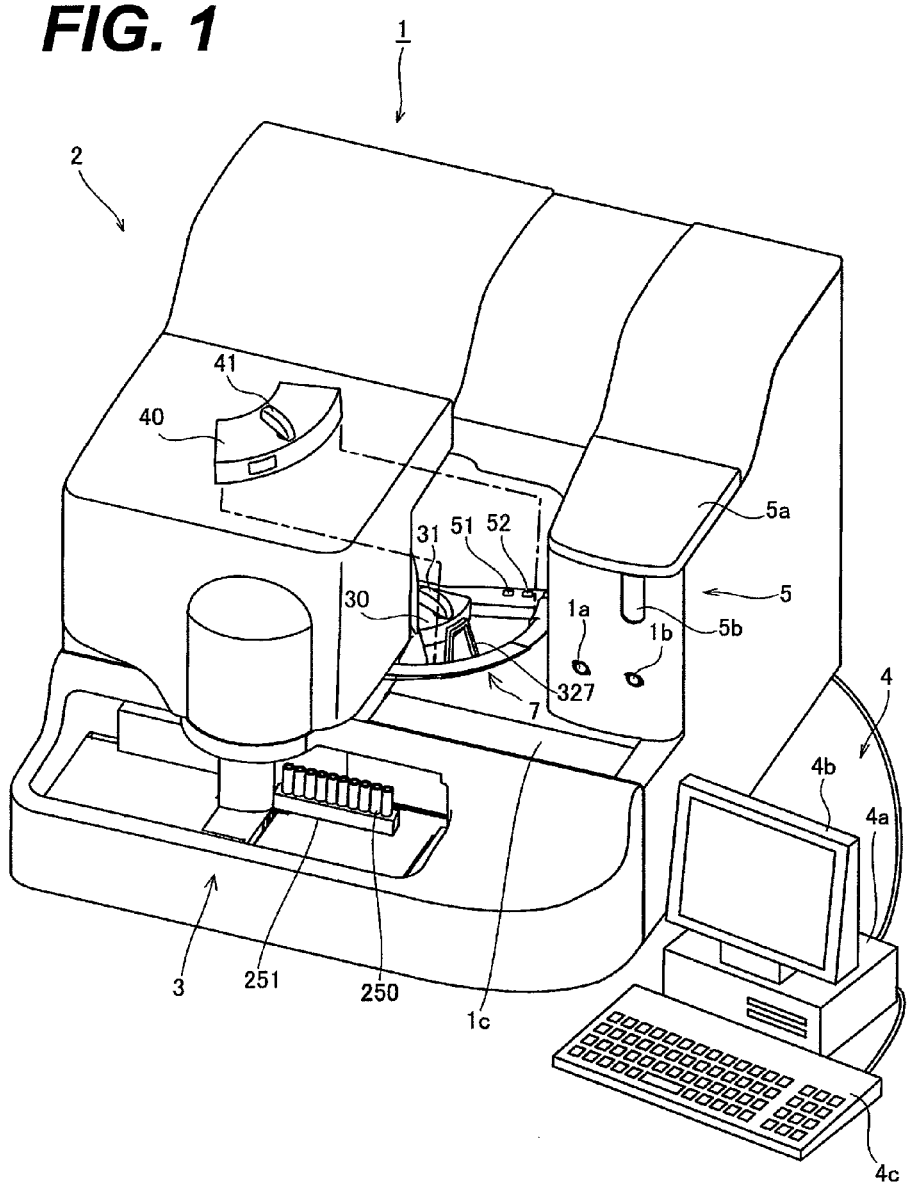
FIG. 1 is a perspective view showing an overall configuration of a sample analyzer according to one embodiment of the present invention.
Figure 2:
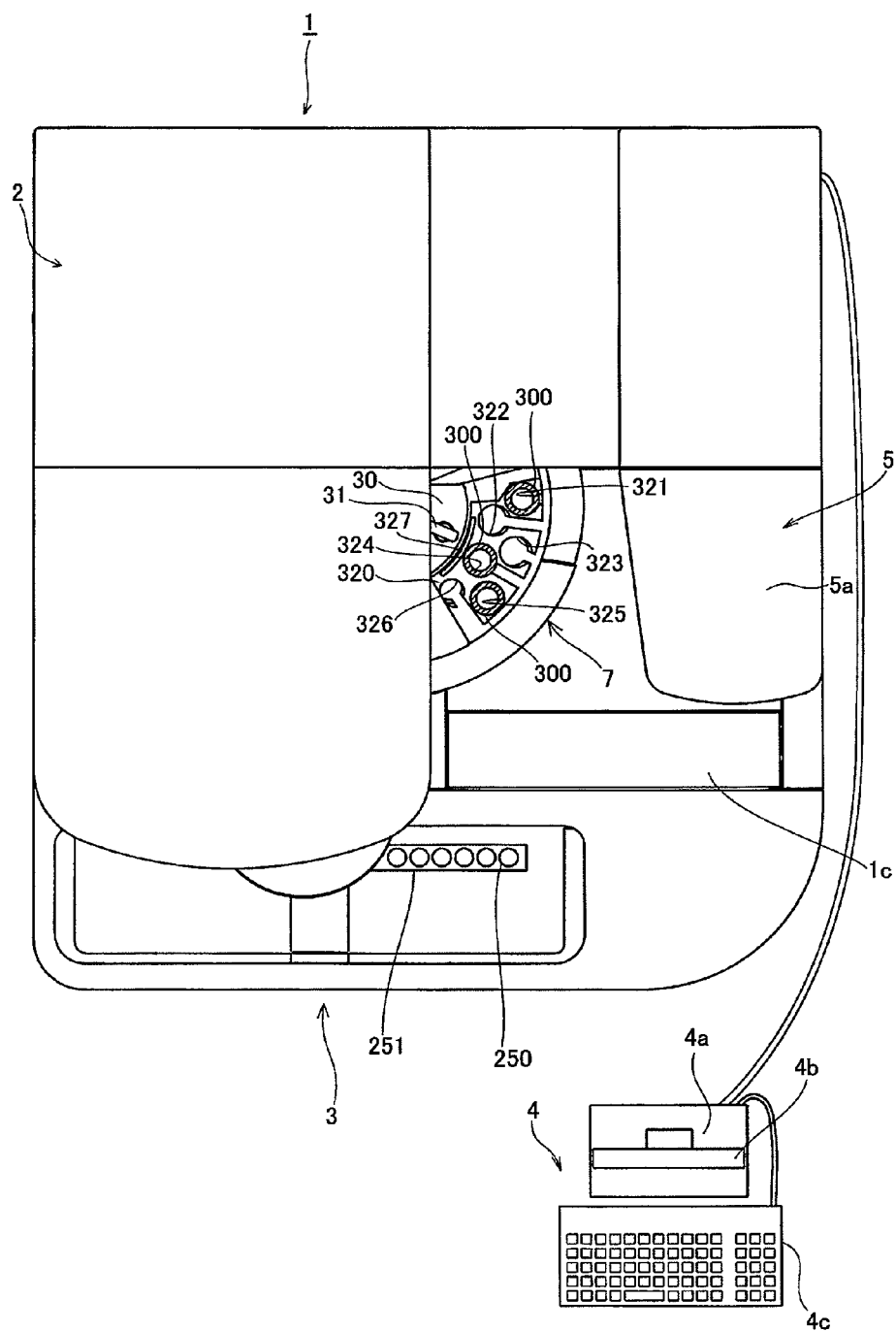
FIG. 2 is a plan view of the sample analyzer shown in FIG. 1.

As shown in FIGS. 1 and 2, the sample analyzer 1 is configured by a measurement mechanism unit 2, a sample conveyance mechanism unit 3 arranged on the front face side of the measurement mechanism unit 2, and a control device 4 electrically connected to the measurement mechanism unit 2. A cuvette inserting section 5 for inserting a cuvette 200 (see FIG. 4), which is the container of the sample when performing the measurement, is arranged in the measurement mechanism unit 2. An openable/closable lid 5a and a window 5b through which the interior of the cuvette inserting section 5 can be seen are formed in the cuvette inserting section 5. An emergency stop button 1a and a measurement start button 1b are arranged on the front face side of the cuvette inserting section 5. The lid 5a (see FIG. 1) is provided to insert the cuvette 200 into a hopper 161a (see FIG. 4) of a cuvette supply mechanism section 160, to be hereinafter described. The user is able to see the remaining amount of the cuvette 200 stored in the hopper 161a (see FIG. 4) through the window 5b. The emergency stop button 1a (see FIG. 1) has a function of stopping the measurement in time of emergency. The measurement start button 1b (see FIG. 1b) has a function of starting the measurement when pushed. The user thus can start the measurement immediately after inserting the cuvette 200. The measurement can also be started or stopped through operation of the control device 4.

As shown in FIGS. 1 and 2, the control device 4 consists of a personal computer 401 (PC), and includes a controller 4a, a display 4b and a keyboard 4c. The controller 4a has a function of transmitting an operation start signal of the measurement mechanism unit 2 to a controller 501 of the measurement mechanism unit 2, to be hereinafter described, and analyzing the optical information of the sample obtained by the measurement mechanism unit 2. The controller 4a is made up of CPU, ROM, RAM, or the like. The display 4b is provided to display information associated with interference substance (hemoglobin, milky fluid (fat), and bilirubin) present in the sample, as well as the analysis result obtained by the controller 4a.

Figure 6:
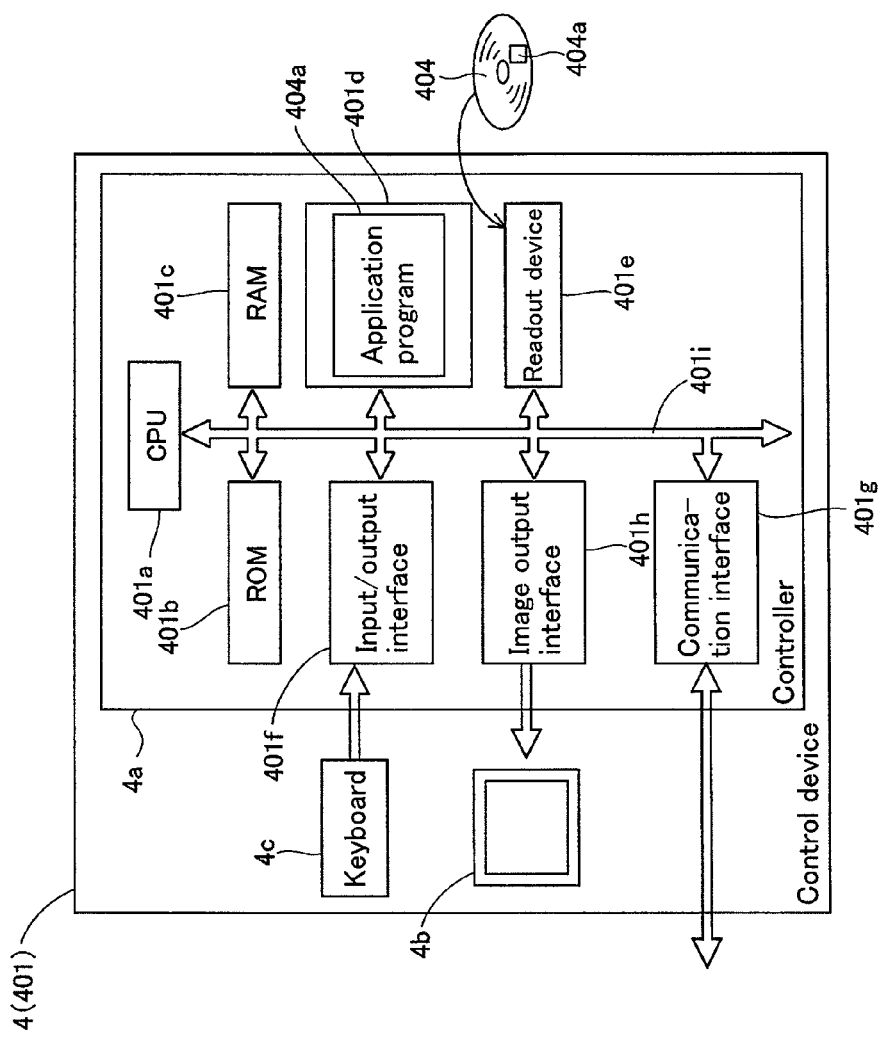
FIG. 6 is a block diagram showing a control device of the sample analyzer according to one embodiment of the present invention.

The configuration of the control device 4 will now be described. As shown in FIG. 6, the controller 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a can execute computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

Figure 32:
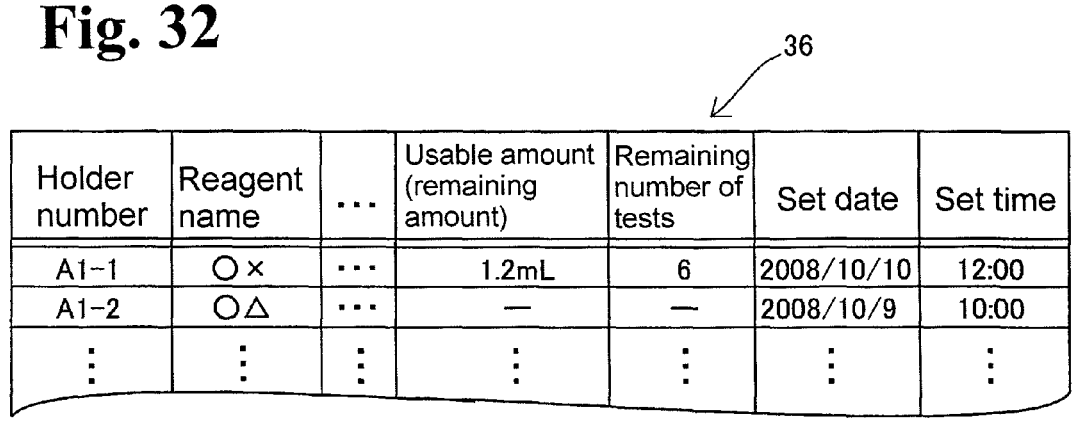
FIG. 32 is a schematic view showing a structure of a reagent information database stored in the hard disc of the sample analyzer according to one embodiment of the present invention.

The hard disc 401d is installed with various computer programs to be executed by the CPU 401a such as operating system and application program, as well as data used in executing the computer program. The application program 404a for performing the display process of the reagent information according to the present embodiment is also installed in the hard disc 401d. In the present embodiment, a table of a reagent master, a reagent lot master, a container master, and the like is also stored in the hard disc 401d. The hard disc 401d stores a reagent information database 36 (see FIG. 32). As shown in FIG. 32, the reagent information database 36 is a relational database, and includes each field of holder number, reagent name, usable amount (remaining amount), remaining number of tests (usable number of times), set date, set time, and the like. Each record corresponds to one reagent of a plurality of reagents placed in the reagent storing part 6 (see FIG. 3). The controller 4a references the table of the reagent master, the reagent lot master, and the container master, to be hereinafter described, stored in the hard disc 401d based on the barcode information read by a reagent barcode reader 350 (see FIG. 3) to acquire the reagent information such as the holder number, the reagent name, the lot number, the kind of reagent container, and the expiration date of the reagent and store the same in the reagent information database 36. The reagent information stored in the reagent information database 36 is reflected on the display 4b by the controller 4a of the control device 4.

The read-out device 401e is configured by flexible disc drive, CD-ROM drive, DVD-ROM drive, and the like, and is able to read out computer programs and data recorded on a portable recording medium 404. The application program 404a according to the present embodiment is stored in the portable recording medium 404, wherein the computer 401 can read out the application program 404a from the portable recording medium 404, and install the application program 404a to the hard disc 401d.

The application program 404a is not only provided by the portable recording medium 404, and may be provided through an electrical communication line (wired or wireless) from external devices communicably connected with the computer 401 by the electrical communication line. For instance, the application program 404a may be stored in the hard disc of the server computer on the Internet, wherein the computer 401 can access the server computer to download the application program 404a and install the application program 404a in the hard disc 401d.

Operating system providing graphical user interface environment such as Windows (registered trademark) manufactured and sold by US Microsoft Co. is installed in the hard disc 401d. In the following description, the application program 404a according to the present embodiment is assumed to be operating on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 can transmit and receive data with the measurement mechanism unit 2 using a predetermined communication protocol by means of the communication interface 401g.

The image output interface 401h is connected to the display 4b configured by LCD, CRT, or the like, and is configured to output the image signal corresponding to the image data provided from the CPU 401a to the display 4b. The display 4b displays the image (screen) according to the input image signal.

Figure 7:
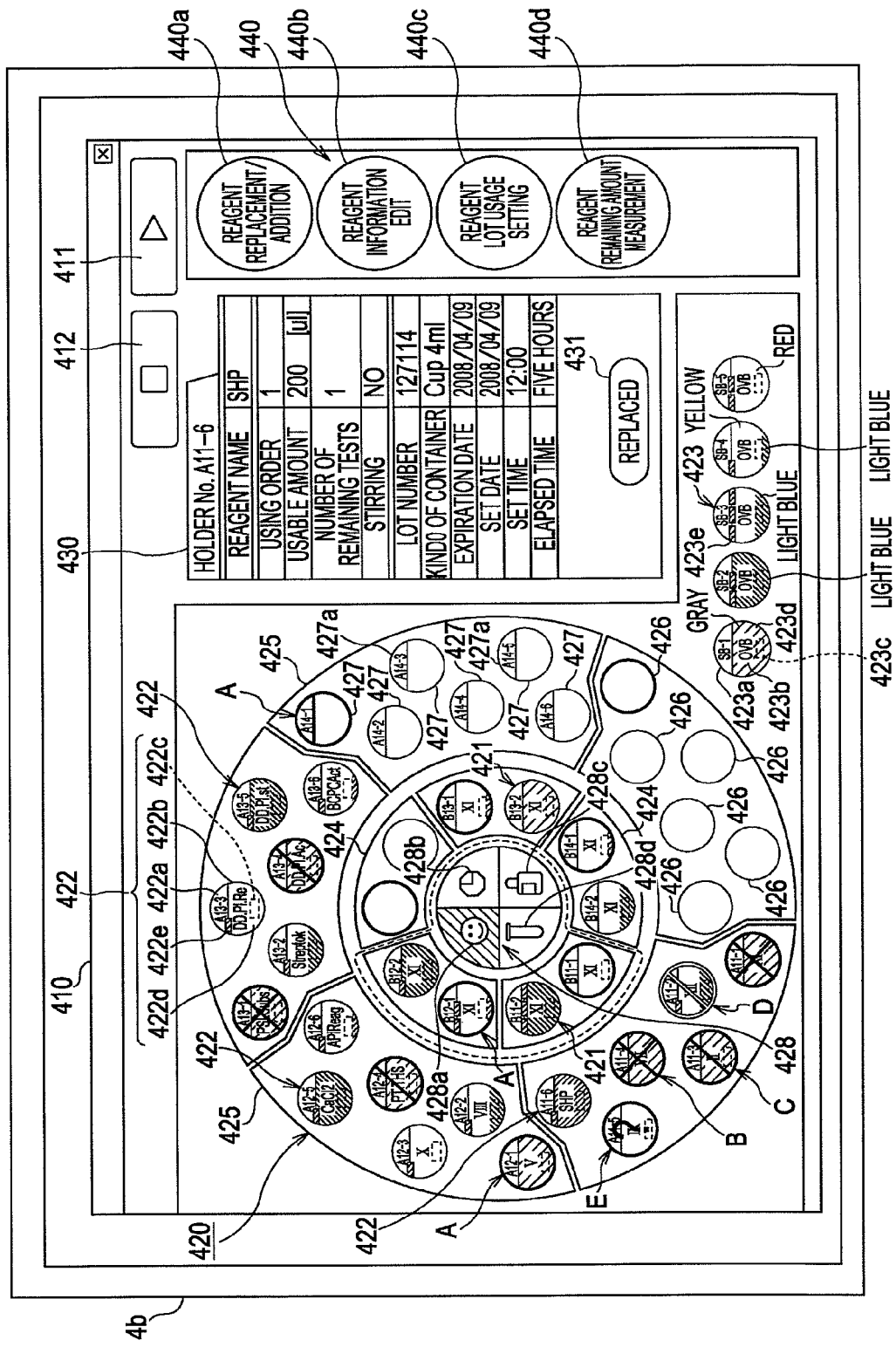
FIG. 7 is a view showing a state in which a no-additional information icon of the reagent management screen according to one embodiment of the present invention is selected.

In the present embodiment, the display 4b can display a reagent management screen 410 for displaying the arrangement of the reagents of the reagent storing part 6, to be hereinafter described, as shown in FIG. 7. The reagent management screen 410 includes a reagent arrangement displaying region 420, a reagent detailed information displaying region 430, and an operation means displaying region 440. The reagent management screen 410 also includes a measurement start button 411 for starting the measurement of the sample analyzer 1, and a measurement stop button 412 for stopping the measurement. The display 4b has a touch panel function, wherein the buttons and the like displayed on the reagent management screen 410 can be selected or operated by being directly touched by the user.

The reagent arrangement displaying region 420 displays, in a specifiable manner, a maximum of ten first reagent marks 421 displayed in correspondence to the arrangement state of the reagent arranged in a first reagent table 11 on the inner side, a maximum of thirty second reagent marks 422 displayed in correspondence to the arrangement state of the reagent arranged in a second reagent table 12 on the outer side, and a maximum of five diluting/cleaning fluid marks 423 displayed in correspondence to the arrangement state of the diluting fluid or the cleaning fluid.

Figure 15:
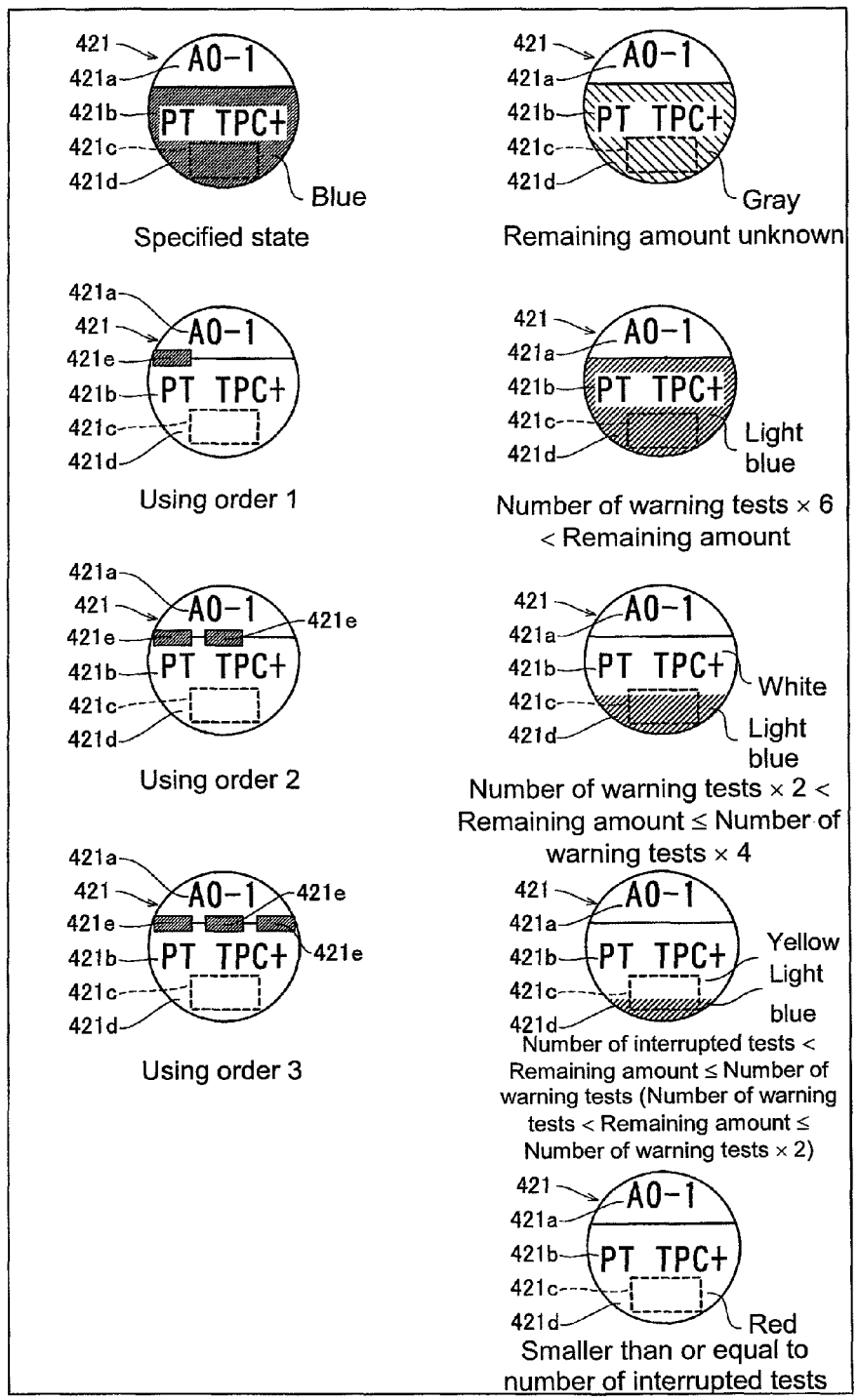
FIG. 15 is a view describing a display of a reagent mark used in the sample analyzer according to one embodiment of the present invention.

As shown in FIG. 15, the first reagent mark 421 includes a position displaying portion 421a showing the position of the reagent arranged in a region of the upper part, a reagent name displaying portion 421b showing the reagent name arranged at a central part, and an additional information displaying portion 421c arranged at a lower part. A remaining amount indicator 421d displaying the remaining amount of the reagent by color is arranged overlapping (as background) the reagent name displaying portion 421b and the additional information displaying portion 421c. In the first reagent mark 421, a using order mark 421e is arranged in a region intermediate (on the boundary line) of the position displaying portion 421a and the reagent name displaying portion 421b. As shown in FIG. 7, the second reagent mark 422 includes a position displaying portion 422a, a reagent name displaying portion 422b, an additional information displaying portion 422c, a remaining amount indicator 422d, and a using order mark 422e, similar to the first reagent mark 421. The diluting/cleaning fluid mark 423 also includes a position displaying portion 423a arranged in a region of the upper part and showing the position of the diluting fluid/cleaning fluid, a fluid name displaying portion 423b showing the fluid name of the diluting fluid/cleaning fluid arranged at a central part, and an additional information displaying portion 423c arranged at a lower part. The diluting/cleaning fluid mark 423 also includes a remaining amount indicator 423d arranged overlapping (as background) the fluid name displaying portion 423b and the additional information displaying portion 423c, and a using order mark 423e arranged in a region intermediate (on the boundary line) of the position displaying portion 421a and the reagent name displaying portion 421b. The diluting fluid/cleaning fluid is sometimes arranged in the first reagent table 11 or the second reagent table 12. In such case, the information of the diluting fluid/cleaning fluid is displayed in the first reagent mark 421 or the second reagent mark 422 corresponding to the arranged position of the diluting fluid/cleaning fluid.

In the present embodiment, the specified first reagent mark 421, the second reagent mark 422, or the diluting/cleaning fluid mark 423 is displayed to be identifiable from the reagent marks or the diluting/cleaning fluid marks other than the specified reagent mark (first reagent mark 421, second reagent mark 422, or diluting/cleaning fluid mark 423). For instance, as shown in FIG. 15, the remaining amount indicator 421d of the specified first reagent mark 421 is displayed in blue ("specified state" of FIG. 15). Display is similarly made in blue even when the second reagent mark 422 or the diluting/cleaning fluid mark 423 is specified. Therefore, in the example shown in FIG. 7, the background (remaining amount indicator 422d) of the reagent name displaying portion 422b (e.g., SHP of second reagent mark 422) and the additional information displaying portion 422c (non-display) of the specified second reagent mark 422 is displayed in blue (illustrated with thin hatching).

Figure 5:
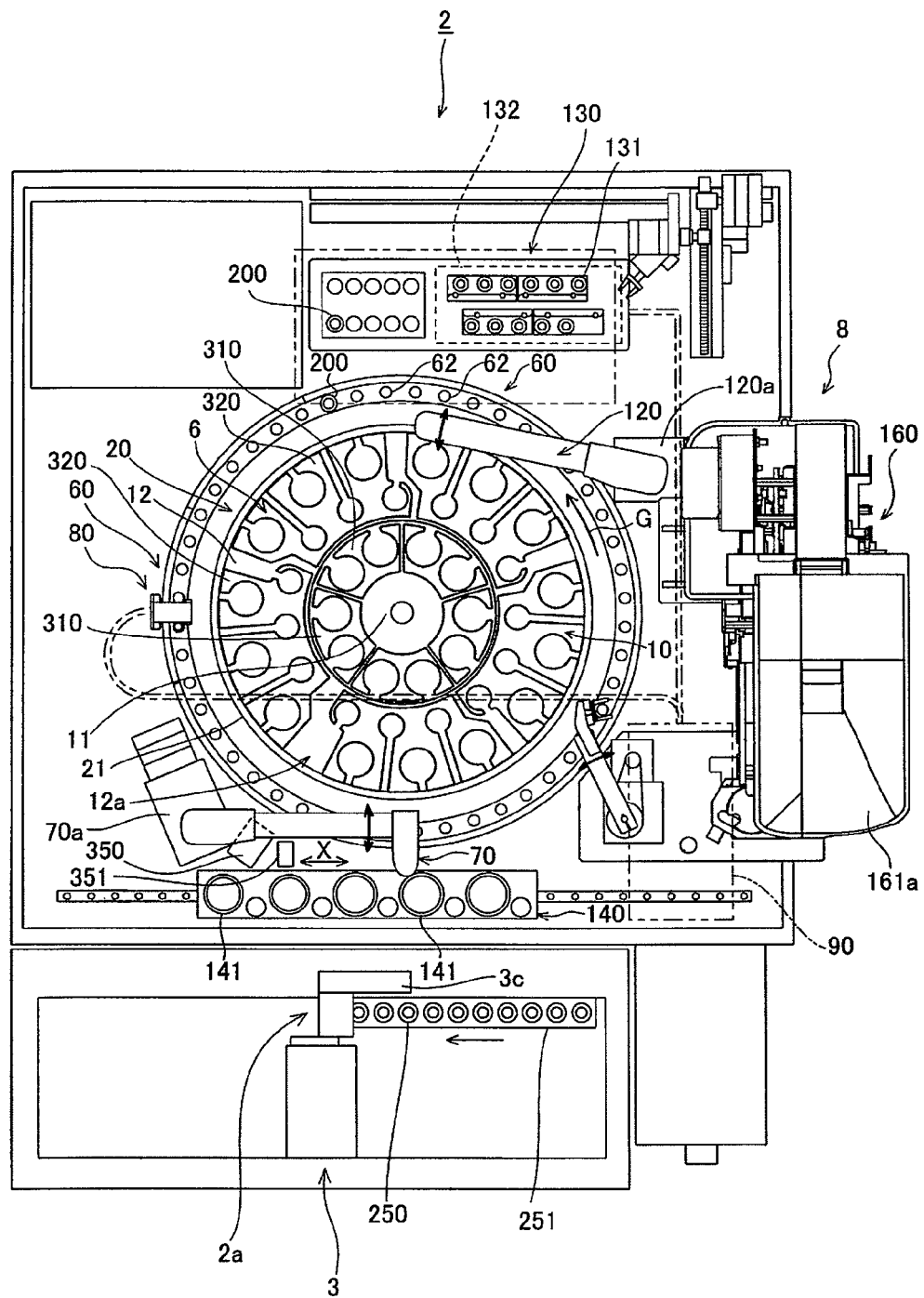
FIG. 5 is a plan view showing the interior of the measurement mechanism unit and the reagent storing part shown in FIG. 4.

The positional information (holder number) of the reagent displayed in the position displaying portions 421a and 422a of the first reagent mark 421 and the second reagent mark 422 is displayed by reading the barcodes 311b, 312b (see FIG. 16) of the first reagent container rack 310 and the barcodes 321b to 326b (see FIG. 17) of the second reagent container rack 320 with the reagent barcode reader 350 (see FIG. 5). The reagent names displayed in the reagent name displaying portions 421b and 422b are displayed with reference to the reagent master (table) to be hereinafter described based on the value of reading the barcode 300a (see FIGS. 18 and 19) of the reagent container 300 accommodating the reagent with the reagent barcode reader 350 (see FIG. 5). The position displaying portion 423a of the diluting/cleaning fluid mark is constantly displayed since a holder 141 (see FIG. 5) of an emergency setting portion 140 for holding the diluting/cleaning fluid container (not shown) accommodating the diluting fluid or the cleaning fluid is fixed to the sample analyzer 1. The fluid name displaying portion 423b is displayed with reference to the reagent master (table) to be hereinafter described based on the value of reading the barcode (not shown) of the diluting/cleaning fluid container (not shown) accommodating the diluting fluid or the cleaning fluid with the reagent barcode reader 351 (see FIG. 5).

In the present embodiment, the additional information displaying portions 421c, 422c, and 423c of each of the first reagent mark 421, the second reagent mark 422 and the diluting/cleaning fluid mark 423 display the reagent information selected by the user in a selection accepting region 428 (see FIG. 7) in a switchable manner as the additional information of each reagent mark. Specifically, the additional information displaying portions 421c, 422c, and 423c display one of the elapsed time from the reagent is arranged in the first reagent table 11, the second reagent table 12 or the holder 141, the remaining amount (usable amount) of the reagent in the reagent container 300 or the diluting/cleaning fluid container (not shown), or the remaining number of tests (usable number of times) of the reagent. The switching of the reagent information displayed in the additional information displaying portions 421c, 422c, and 423c is accepted by selecting an elapsed time icon 428b, a reagent remaining amount icon 428c, or a remaining number of tests icon 428d. The display of the additional information displaying portions 421c, 422c, and 423c may be set to non-display. This is accepted by selecting no additional information icon 428a of the selection accepting region 428.

Figure 8:
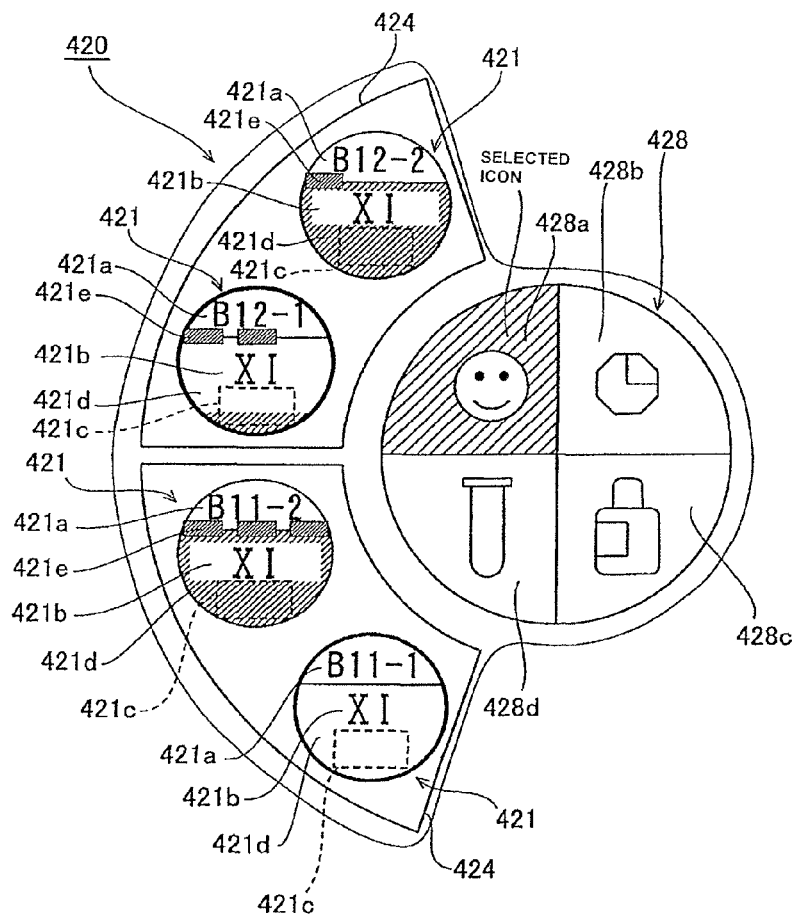
FIG. 8 is an enlarged view of the reagent management screen shown in FIG. 7.
Figure 9:
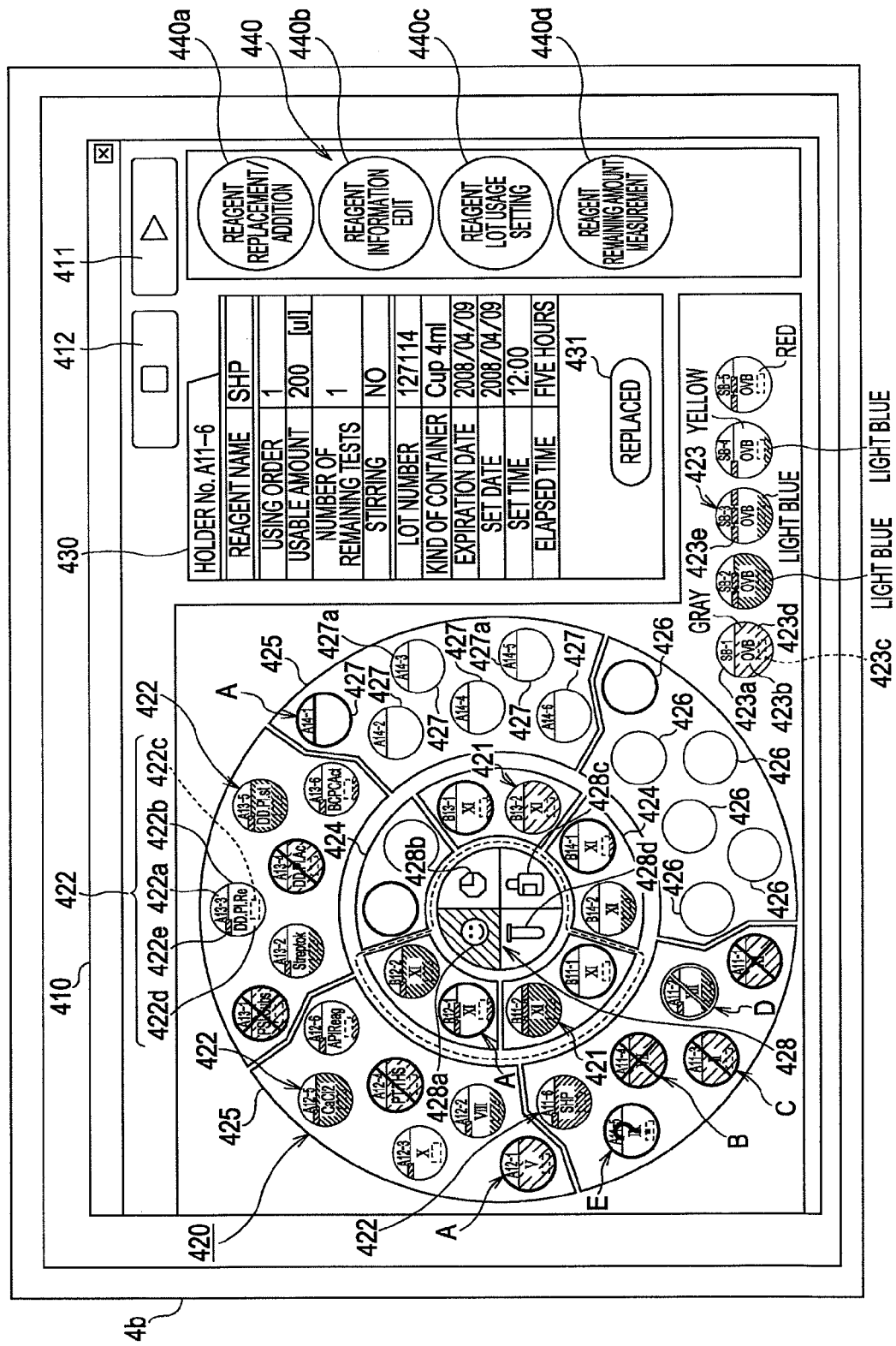
FIG. 9 is a view showing a state in which an elapsed time icon of the reagent management screen according to one embodiment of the present invention is selected.
Figure 10:
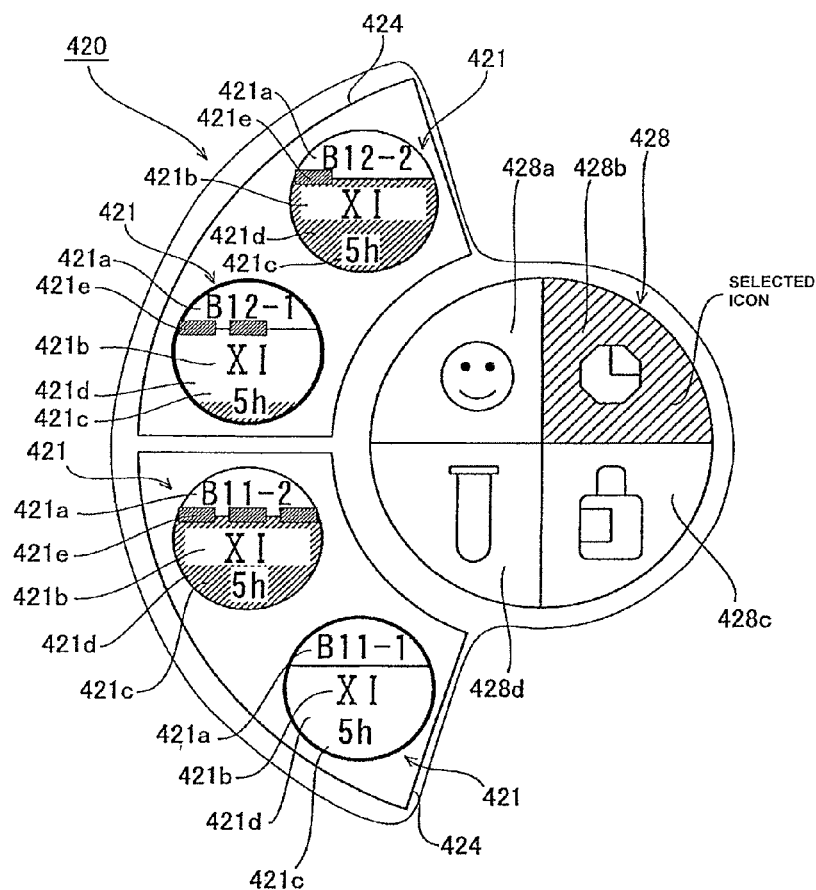
FIG. 10 is an enlarged view of the reagent management screen shown in FIG. 9.
Figure 11:
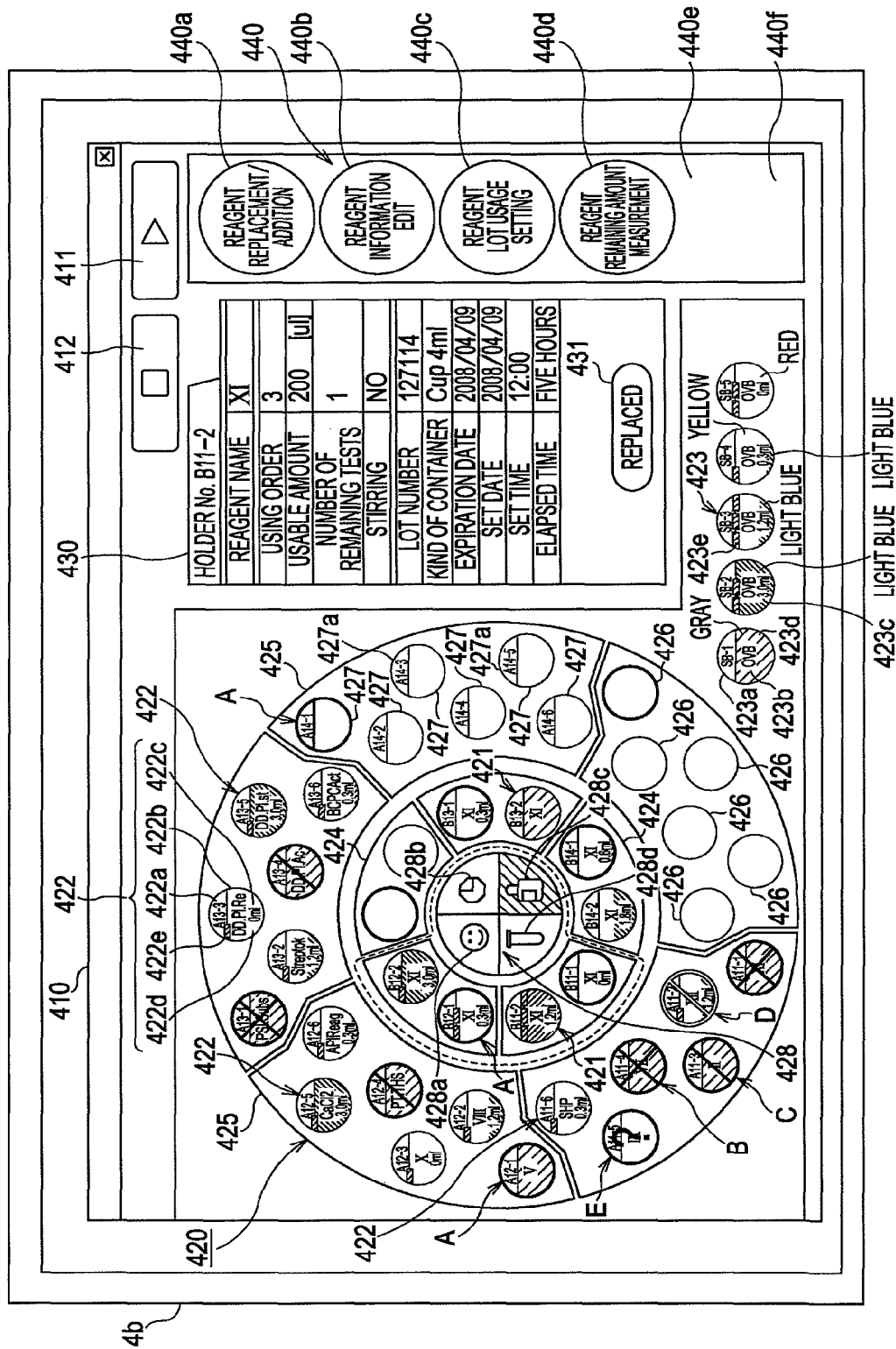
FIG. 11 is a view showing a state in which a reagent remaining amount icon of the reagent management screen according to one embodiment of the present invention is selected.
Figure 12:
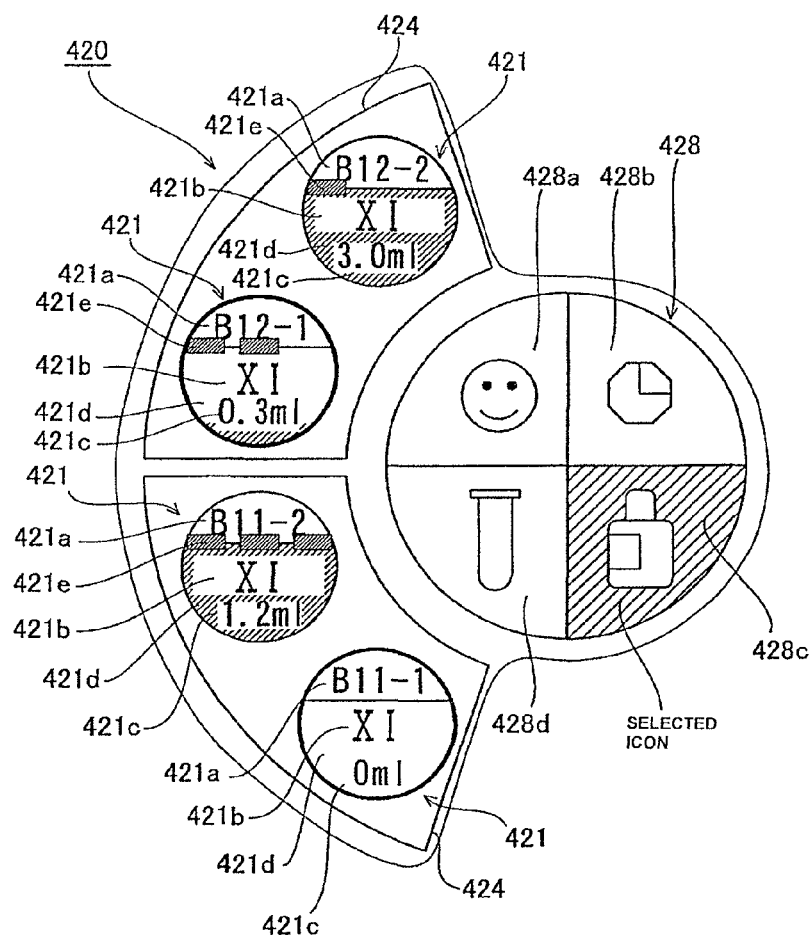
FIG. 12 is an enlarged view of the reagent management screen shown in FIG. 11.

The display switching of the reagent information by the additional information displaying portion 421c will be specifically described with the additional information displaying portion 421c of the first reagent mark 421 by way of example. As shown in FIGS. 7 and 8, if the no additional information icon 428a is selected, the additional information displaying portion 421c of the first reagent mark 421 is set to non-display (see broken line part). As shown in FIGS. 9 and 10, if the elapsed time icon 428b is selected, the elapsed time from the time point where the barcode 300a (see FIG. 18) of the reagent container 300 of the reagent corresponding to the first reagent mark 421 is read by the reagent barcode reader 350 (see FIG. 5) until the current time point is displayed. Here, "5 h" is displayed in each additional information displaying portion 421c of the four first reagent marks 421 shown in FIG. 10, indicating that five hours elapsed from the barcode 300a of the reagent container 300 is read. As shown in FIGS. 11 and 12, if the reagent remaining amount icon 428c is selected, the remaining amount (usable amount) of the reagent stored in the reagent container 300 corresponding to each first reagent mark 421 is displayed. Here, "3.0 ml", "0.3 ml", "1.2 ml", and "0 ml" are displayed in each additional information displaying portion 421c of the four first reagent marks 421 shown in FIG. 12, indicating that the remaining amount of the reagent stored in the respective reagent container 300 corresponding to each first reagent mark 421 is "3.0 ml", "0.3 ml", "1.2 ml", and "0 ml".

Figure 13:
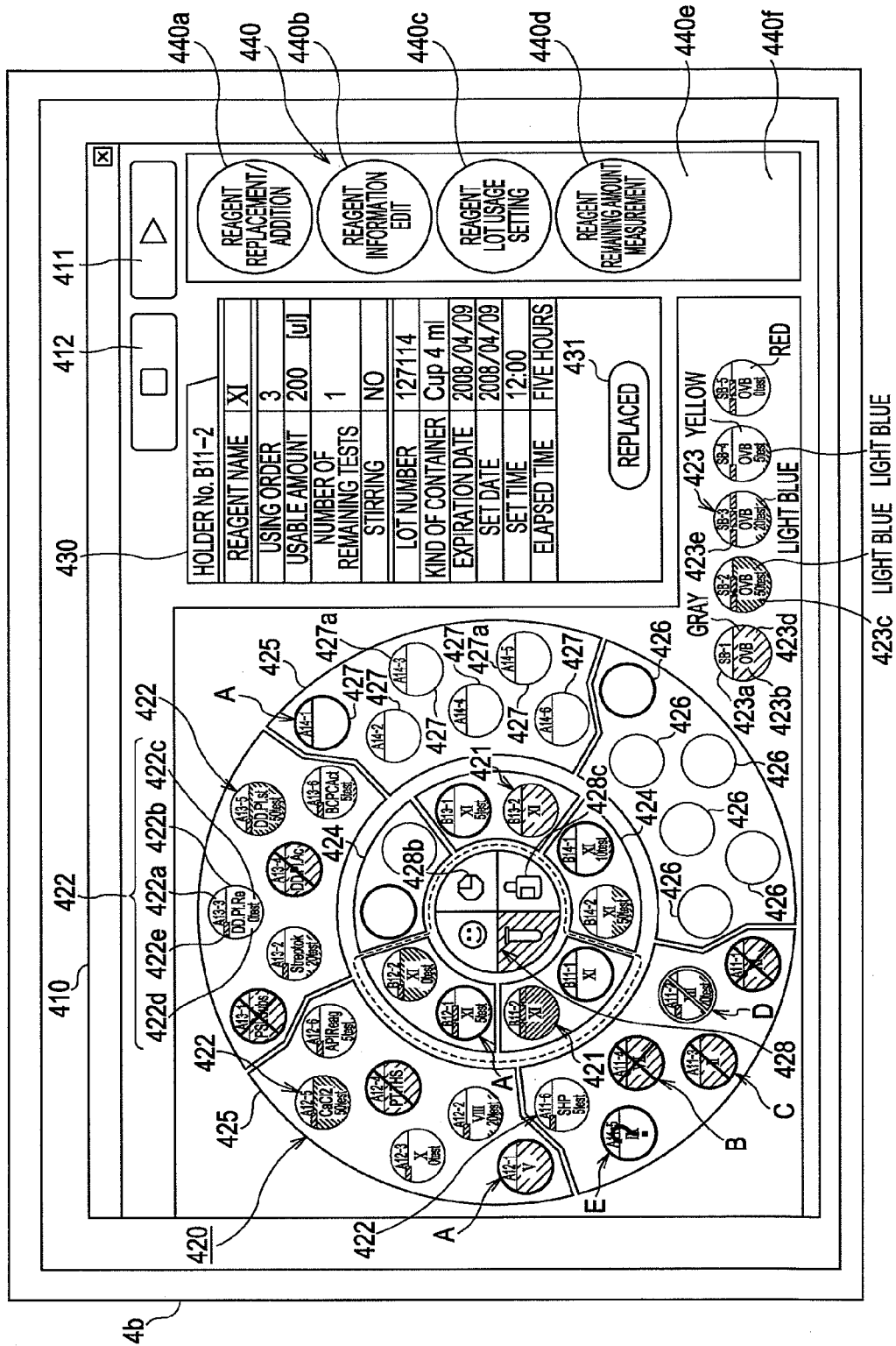
FIG. 13 is a view showing a state in which a remaining number of tests icon of the reagent management screen according to one embodiment of the present invention is selected.
Figure 14:
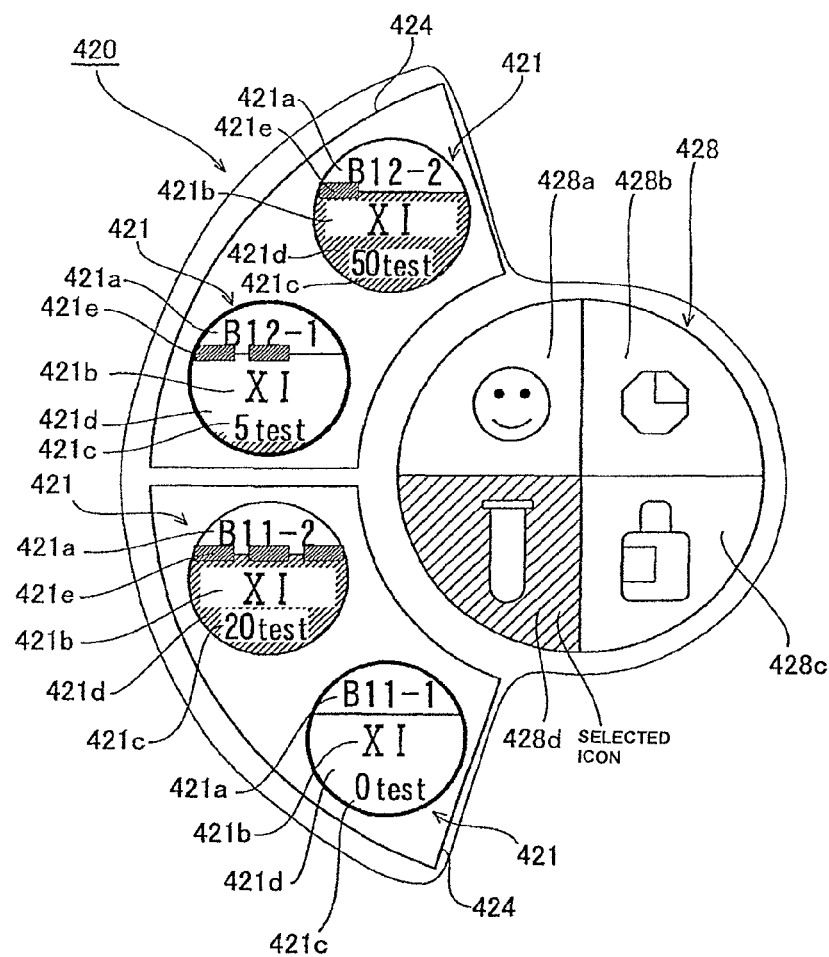
FIG. 14 is an enlarged view of the reagent management screen shown in FIG. 13.

Furthermore, as shown in FIGS. 13 and 14, if the remaining number of tests icon 428d is selected, a value (remaining number of tests) of dividing the remaining amount (usable amount) of the reagent stored in the reagent 300 corresponding to each first reagent mark 421 by the using amount of reagent necessary for one measurement set in advance in the reagent master is displayed. Here, "50 tests", "5 tests", "20 tests", and "0 test" are displayed in each additional information displaying portion 421c of the four first reagent marks 421 shown in FIG. 14, indicating that the remaining number of tests of the reagent stored in the respective reagent container 300 corresponding to each first reagent mark 421 is "50 times", "5 times", "20 times", and "0 time". The additional information displaying portion 421c of the first reagent mark 421 has been described herein, but the additional information displaying portions 422c and 423c of the second reagent mark 422 and the diluting/cleaning fluid mark 423 are also similarly displayed.

In the present embodiment, as shown in FIG. 15, the remaining amount display of the reagent or the diluting fluid/cleaning fluid by the remaining amount indicators 421d, 422d, and 423d is displayed by color corresponding to the remaining amount in the container. The first reagent mark 421 will be described by way of example. The remaining amount indicator 421d displays the "remaining number of tests" obtained by dividing the reagent remaining amount in the container or the "usable amount" by the reagent amount used in one measurement as an index. The display of the remaining amount indicator 421d is displayed by changing the color with the number of interrupted tests (e.g., remaining number of tests of five times) and the number of warning tests (e.g., remaining number of tests of zero time) set by the user as a reference.

Specifically, as shown in FIG. 15, if the remaining number of tests is greater than six times the number of warning tests, the remaining amount is sufficiently ensured in the reagent container 300, and thus the entire background of the reagent name displaying portion 421b and the additional information displaying portion 421c of the first reagent mark 421 is displayed in light blue. If the remaining number of tests is smaller than or equal to six times the number of warning tests, the light blue region of the remaining amount indicator 421d decreases in a stepwise manner (white region increases) according to the decrease in the reagent remaining amount. For instance, if the remaining number of tests is greater than twice the number of warning tests and smaller than or equal to four times the number of warning tests, the light blue region decreases below the reagent name displaying portion 421b. If the remaining number of tests of the reagent is greater than the number of interrupted tests and smaller than or equal to the number of warning tests, the light blue region showing the reagent of the remaining amount indicator 421d further decreases, and the warning color of yellow is displayed. If the remaining number of tests of the reagent is smaller than or equal to the number of interrupted tests, the light blue region of the remaining amount indicator 421d is in non-display, and the warning color of red indicating rundown of the reagent is displayed. If the remaining amount of the reagent is unknown, the remaining amount indicator 421d is displayed in gray. The remaining amount indicator 421d is displayed in an overlapping manner as the background of the reagent name displaying portion 421b and the additional information displaying portion 421c of the first reagent mark 421. Thus, the remaining amount indicator 421d is displayed even if the display of the additional information displaying portion 421c is switched to non-display or to other displays. Therefore, the remaining amount indicators 421d, 422d, and 423d of each of the first reagent mark 421, the second reagent mark 422, and the diluting/cleaning fluid mark 423 display the remaining amount of the reagent by changing the color according to the remaining amount of the reagent in the container.

The remaining amount of reagent in the reagent container 300 is calculated by the shape of the reagent container 300 and the height of the liquid level of the reagent stored in the reagent container 300 specified with reference to the container master (table) based on the value read by the reagent barcode reader 350 from the barcode 300a of the reagent container 300. The remaining amount of the diluting fluid or the cleaning fluid displayed in the remaining amount indicator 423d of the diluting/cleaning fluid mark 423 is calculated by the shape of the diluting/cleaning fluid container and the height of the liquid level of the diluting fluid or the cleaning fluid stored in the diluting/cleaning fluid container specified with reference to the container master (table) based on the value read by the reagent barcode reader 351 from the barcode (not shown) of the diluting/cleaning fluid container (not shown).

The using order marks 421e, 422e, and 423e of each of the first reagent mark 421, the second reagent mark 422 and the diluting/cleaning fluid mark 423 display the order used in the measurement if the reagent of the same kind (e.g., "PTTPC+" etc.) is arranged in plurals in the first reagent table 11 or the second reagent table 12 (include holder 141 in the case of the diluting fluid/cleaning fluid). The using order is set in the order of earlier "set date" and "set time", which are the date and time the barcode 300a (see FIG. 18) of the reagent container 300 is read by the reagent barcode reader 350 (see FIG. 5). A maximum of three using order marks 421e, 422e, and 423e are displayed, wherein the number of using order mark represents the using order. Showing the first reagent mark 421 by way of example, one using order mark 421e is displayed in a region between the position displaying portion 421a and the reagent name displaying portion 421b in the first reagent mark 421 (using order 1) corresponding to the reagent to be used the first, as shown in FIG. 15. Two using order marks 421e are displayed in a region between the position displaying portion 421a and the reagent name displaying portion 421b in the first reagent mark 421 (using order 2) corresponding to the reagent to be used the second. Three using order marks 421e are displayed in a region between the position displaying portion 421a and the reagent name displaying portion 421b in the first reagent mark 421 (using order 3) corresponding to the reagent to be used the third. If the same reagent ("PTTPC+" in FIG. 15) is arranged in plurals by four or more in the reagent table, the using order after the third using order is not displayed. When the reagent of the using order 1 is replaced and a new reagent is set, the "set date" and the "set time" are updated to the date and time of the reading of the barcode 300a. The using order thus moves up, and three using order marks 421e are displayed to the reagent mark corresponding to the fourth using order.

As shown in FIG. 7, in the reagent arrangement displaying region 420, the first reagent mark 421 is displayed by being divided by twos for every first rack mark 424 corresponding to five first reagent container racks 310 (see FIG. 5) capable of holding two reagent containers 300 arranged in the first reagent table 11 (see FIG. 5). The second reagent mark 422 is displayed by being divided by sixes for every second rack mark 425 corresponding to five second reagent container racks 320 (see FIG. 5) capable of holding six reagent containers 300 arranged in the second reagent table 12 (see FIG. 5). In other words, at which position of which reagent container rack (first reagent container rack 310 or second reagent container rack 320) of which reagent table (first reagent table 11 or second reagent table 12) the reagent is placed can be checked in the reagent management screen 410.

If the reagent container rack is not arranged in the reagent table, a circular no-rack arrangement mark 426, where display is not made on the inner side, is displayed at a region corresponding to the portion where the reagent container rack is not arranged. If the first reagent container rack 310 or the second reagent container rack 320 is arranged in the first reagent table 11 or the second reagent table 12, and the reagent container 300 to be held in the reagent container rack is not present, a no-reagent arrangement mark 427 is displayed at a region corresponding to the portion where reagent is not arranged. The no-reagent arrangement mark 427 includes a position displaying portion 427a for displaying the positional information (holder number) of the portion not placed with the reagent. This will be hereinafter described in detail.

As shown in FIG. 7, a mark positioned at a predetermined position of the first reagent mark 421, the second reagent mark 422, the no-rack arrangement mark 426, and the no-reagent arrangement mark 427 has the outer periphery of the mark displayed with a predetermined color (e.g., brown (illustrated with heavy line in the figure)). The mark A where outer periphery is displayed in brown indicates that the reagent placed at the relevant position can be stirred. The reagent that requires stirring is placed at the position of the mark A where outer periphery is displayed in brown.

If the reagent that requires stirring is not placed at the position of the mark A where outer periphery is displayed in brown, an error arrangement mark B (e.g., red×mark) is displayed at the reagent mark of the reagent that requires stirring. An expired mark C (one red (illustrated with heavy line in the figure) diagonal line) is displayed at the reagent mark of the expired reagent. The sample analyzer 1 is configured such that the reagent corresponding to the reagent mark displayed with the error arrangement mark or the expired mark is not used for the measurement. A stabilization time expired mark D (e.g., one yellow (illustrated with outlined line in the figure) diagonal line) is displayed at the reagent mark of the reagent a predetermined time (e.g., eight hours) has elapsed from the set date and the set time of the reagent, to be described below. If the reading of the barcode 300a of the reagent container 300 by the reagent barcode reader 350 fails, a barcode reading error mark E (e.g., "?" mark) is displayed at the reagent mark of the reagent stored in the reagent container which reading failed.

In the present embodiment, the circular selection accepting region 428 including four icons (no-additional information icon 428a, elapsed time icon 428b, reagent remaining amount icon 428c, and remaining number of tests icon 428d) image displayed for switching the additional information (reagent information) displayed in each reagent mark is displayed at the middle of the reagent arrangement displaying region 420. The reagent arrangement displaying region 420 includes an annular schematic view showing the first reagent table 11 and the second reagent table 12 configured to an annular form (see FIG. 5), and is arranged to surround the selection accepting region 428. When each icon is selected (pushed), the selection of the reagent information displayed at the additional information displaying portions 421c, 422c, and 423c of the first reagent mark 421, the second reagent mark 422, and the diluting/cleaning fluid mark 423 is accepted. In any case, the holder number and the reagent name are displayed.

The elapsed time icon 428b, the reagent remaining amount icon 428c, and the remaining number of tests icon 428d each has a function selectively displaying, in a switchable manner, the elapsed time, the remaining amount (usable amount), and the remaining number of tests of each reagent in the additional information displaying portions 421c, 422c, and 423c. The no-additional information icon 428a has a function of non-displaying the reagent information displayed at the additional information displaying portions 421c, 422c, and 423c. When one of the icons (no-additional information icon 428a, elapsed time icon 428b, reagent remaining amount icon 428c, and remaining number of tests icon 428d) is selected, the background color of the selected icon is changed (e.g., orange). Thus, the selected icon is displayed identifiable from other icons, so that the kind of reagent information displayed in the additional information displaying portions 421c, 422c, and 423c of each reagent mark (first reagent mark 421, second reagent mark 422, and diluting/cleaning fluid mark 423) can be recognized. When each icon is selected, the selected content thereof (which icon is selected) is stored in the hard disc 401d. Thus, when the task of the sample analyzer 1 is terminated and shut down with each icon selected, the selected content before the shut down is held (displayed) in the next startup.

As shown in FIGS. 7 and 8, when the no-additional information icon 428a is selected by the user, the background color of the no-additional information icon 428a is changed, and the display of the additional information displaying portions 421c, 422c, and 423c of all the marks of the first reagent mark 421, the second reagent mark 422, and the diluting/cleaning fluid mark 423 is non-displayed.

As shown in FIGS. 9 and 10, when the elapsed time icon 428b is selected by the user, the background color of the elapsed time icon 428b is changed, and the display of all the marks is switched to "elapsed time".

As shown in FIGS. 11 and 12, when the reagent remaining amount icon 428c is selected by the user, the background color of the reagent remaining amount icon 428c is changed, and the display of all the marks is switched to "reagent remaining amount (usable amount)".

As shown in FIGS. 13 and 14, when the remaining number of tests icon 428d is selected by the user, the background color of the remaining number of tests icon 428d is changed, and the display of all the marks is switched to "remaining number of tests".

Each reagent information of "elapsed time", "remaining number of tests", and "usable amount" is acquired as the detailed information of each reagent, and stored in the reagent information database 36 of the hard disc 401d. When each icon (no-additional information icon 428a, elapsed time icon 428b, reagent remaining amount icon 428c, and remaining number of tests icon 428d) is selected, the reagent information (elapsed time, usable amount, remaining number of tests) corresponding to the selected icon is read out from the reagent information database 36 of the hard disc 401d, and reflected on each additional information displaying portion 421c, 422c, and 423c.

As shown in FIG. 7, the reagent detailed information displaying region 430 displays the detailed information (holder number, reagent name, using order, remaining amount (usable amount) of reagent, remaining number of tests, presence of stirring, lot number, kind of reagent container, expiration date of reagent, set date, set time, elapsed time, and the like) of the reagent corresponding to the specified first reagent mark 421 or the second reagent mark 422. More specifically, the positional information of the reagent displayed at the position displaying portion of the specified reagent mark is displayed in the field of "holder number". Similar to the reagent name displaying portion of the specified reagent mark, the reagent name specified with reference to the reagent master based on the value read from the barcode 300a of the reagent container 300 by the reagent barcode reader 350 is displayed in the field of "reagent name". The order of use in the measurement when the same reagent is arranged in plurals in the reagent table is displayed in the field of "using order". The remaining amount of the reagent corresponding to the specified reagent mark is displayed in the field of "usable amount". The value of dividing the "usable amount" by the reagent amount necessary for one measurement is displayed in the field of "remaining number of tests". Whether or not the reagent corresponding to the specified reagent mark needs to be stirred is displayed in the field of "stirring". The lot number specified with reference to the reagent lot master based on the value read from the barcode 300a of the reagent container 300 by the reagent barcode reader 350 is displayed in the field of "lot number". The kind of container specified with reference to the container master based on the value read from the barcode 300a of the reagent container 300 by the reagent barcode reader 350 is displayed in the field of "kind of container". The expiration date corresponding to the lot number specified with reference to the reagent lot master based on the value read from the barcode 300a of the reagent container 300 by the reagent barcode reader 350 is displayed in the field of "expiration date". The date and time at which the reagent corresponding to the specified reagent mark is set in the sample analyzer 1 are displayed in the field of "set date" and the field of "set time". The elapsed time from the "set date" and the "set time" at which the reagent is set in the sample analyzer 1 is displayed in the field of "elapsed time". The user can manage the reagent such as judging the replacement timing of the reagent by such detailed information of the reagent. When the reading of the barcode failed and the detailed information of the reagent cannot be displayed, the detailed information of the reagent can be edited by a reagent information edit button 440b. When the remaining amount of reagent is unknown such as immediately after the replacement of the reagent, the remaining amount can be measured with a reagent remaining amount measurement button 440d, to be hereinafter described.

The reagent detailed information displaying region 430 also includes "replaced" button 431. The "replaced" button 431 has a function of manually enabling the sample analyzer 1 to recognize that the reagent has been replaced when the replaced reagent is not recognized by the sample analyzer 1 although the reagent is replaced. When the "replaced" button 431 is pushed, the "set date" and the "set time" of the reagent information database 36 are updated to the date and time the "replaced" button 431 is pushed with respect to the corresponding reagent, and the "set date" and the "set time" of the reagent detailed information displaying region 430 are updated to the date and time the "replaced" button 431 is pushed.

The operation means displaying region 440 includes replacement/addition instructing button 440a for instructing replacement or addition of reagent, an edit button 440b for editing the reagent information, a reagent lot setting button 440c for assigning the reagent lot to the measurement lot, and a reagent remaining amount check button 440d.

The sample analyzer 1 is configured such that the first reagent container rack 310 or the second reagent container rack 320 holding the reagent container 300 accommodating the reagent corresponding to the specified reagent mark moves to a predetermined rack retrieving position when the replacement/addition instructing button 440a is selected with the first reagent mark 421 or the second reagent mark 422 specified. When the reagent is to be added, the replacement/addition instructing button 440a is selected with the no-reagent arrangement mark 427 specified. The first reagent container rack 310 or the second reagent container rack 320 corresponding to the rack mark including the specified no-reagent arrangement mark is thereby moved to the rack retrieving position. Similarly, the diluting fluid or the cleaning fluid can be replaced or added by selecting the replacement/addition button 440a with the diluting/cleaning fluid mark 423 specified.

The sample analyzer 1 has a function of color displaying, so as to be identifiable to the user, a standby state until the reagent container rack corresponding to the rack mark including the specified first reagent mark 421, the second reagent mark 422, or the no-reagent arrangement mark 427 is moved to the rack retrieving position from the replacement/addition button 440a is pushed when replacing or adding the reagent, and a retrievable state in which the reagent container rack can be retrieved to the outside from the retrieving position. The replacement and the addition of the reagent will be hereinafter specifically described in detail.

The detailed information of the reagent corresponding to the specified reagent mark can be edited by pushing the edit button 440b with the reagent mark specified. The reagent lot usage setting button 440c has a function of displaying a reagent lot usage setting dialogue (not shown) for setting whether each lot or the combination of lots is usable with respect to a plurality of reagent lots or a combination of a plurality of reagents lots for every measurement item. The reagent remaining amount check button 440d is provided to instruct the device to detect the remaining amount when the reagent which remaining amount is unknown is installed.

Figure 3:
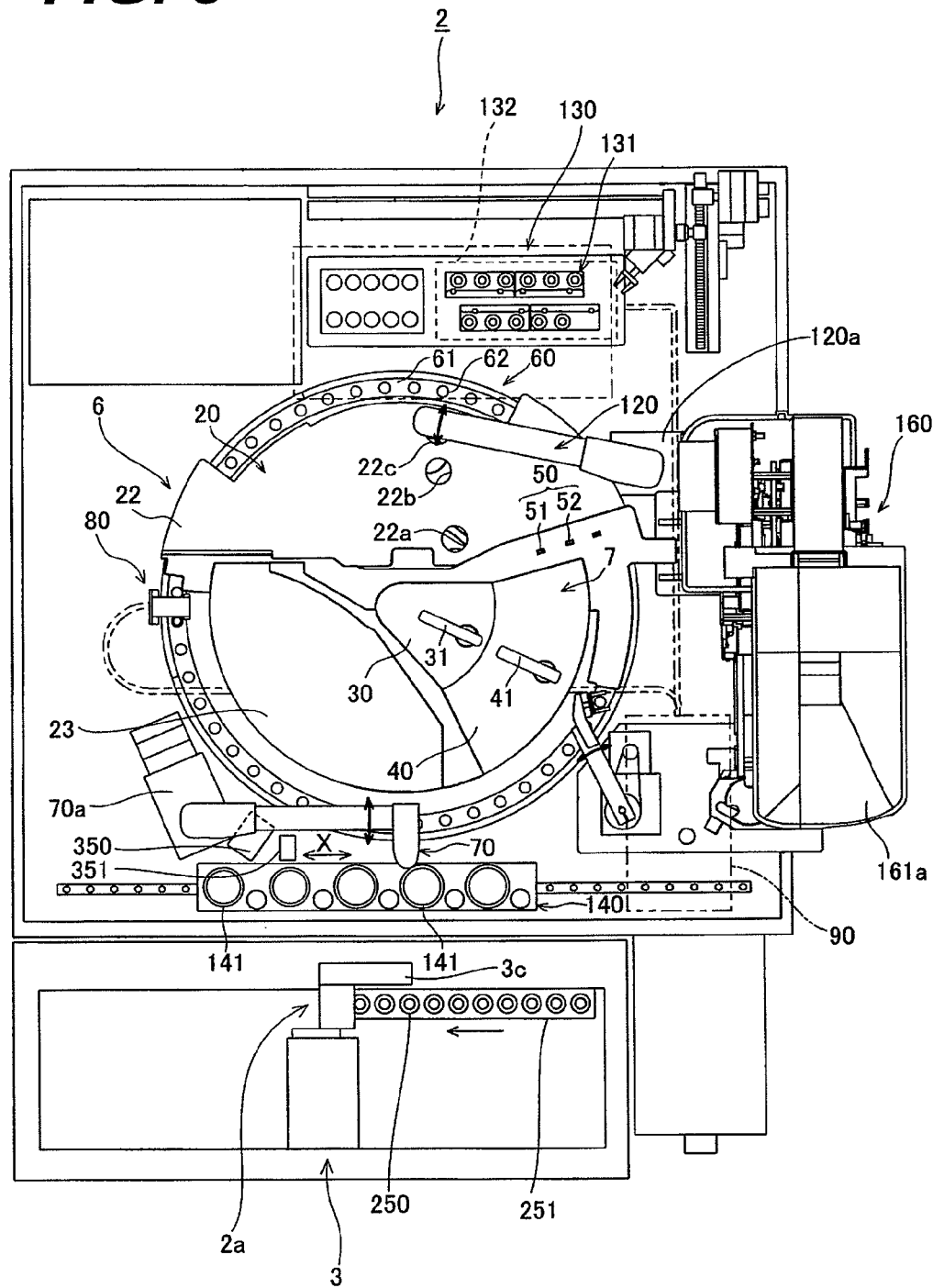
FIG. 3 is a plan view showing a measurement mechanism unit of the sample analyzer according to one embodiment of the present invention.

As shown in FIGS. 1 to 3, the sample conveyance mechanism unit 3 has a function of conveying a rack 251 mounted with a plurality of (ten in the present embodiment) test tubes 250 accommodating a sample to an aspirating position 2a (see FIG. 3) of the measurement mechanism unit 2 to supply the sample to the measurement mechanism unit 2.

The measurement mechanism unit 2 is configured to acquire the optical information related to the supplied sample by performing an optical measurement with respect to the sample supplied from the conveyance mechanism unit 3. In the present embodiment, the optical measurement is performed on the sample dispensed into the cuvette 200 of the measurement mechanism unit 2 from the test tube 250 mounted in the rack 251 of the conveyance mechanism unit 3. As shown in FIG. 3, the measurement mechanism unit 2 includes a reagent storing part 6 for storing reagent, and a reagent replacing part 7 for replacing or adding reagent.

Figure 20:
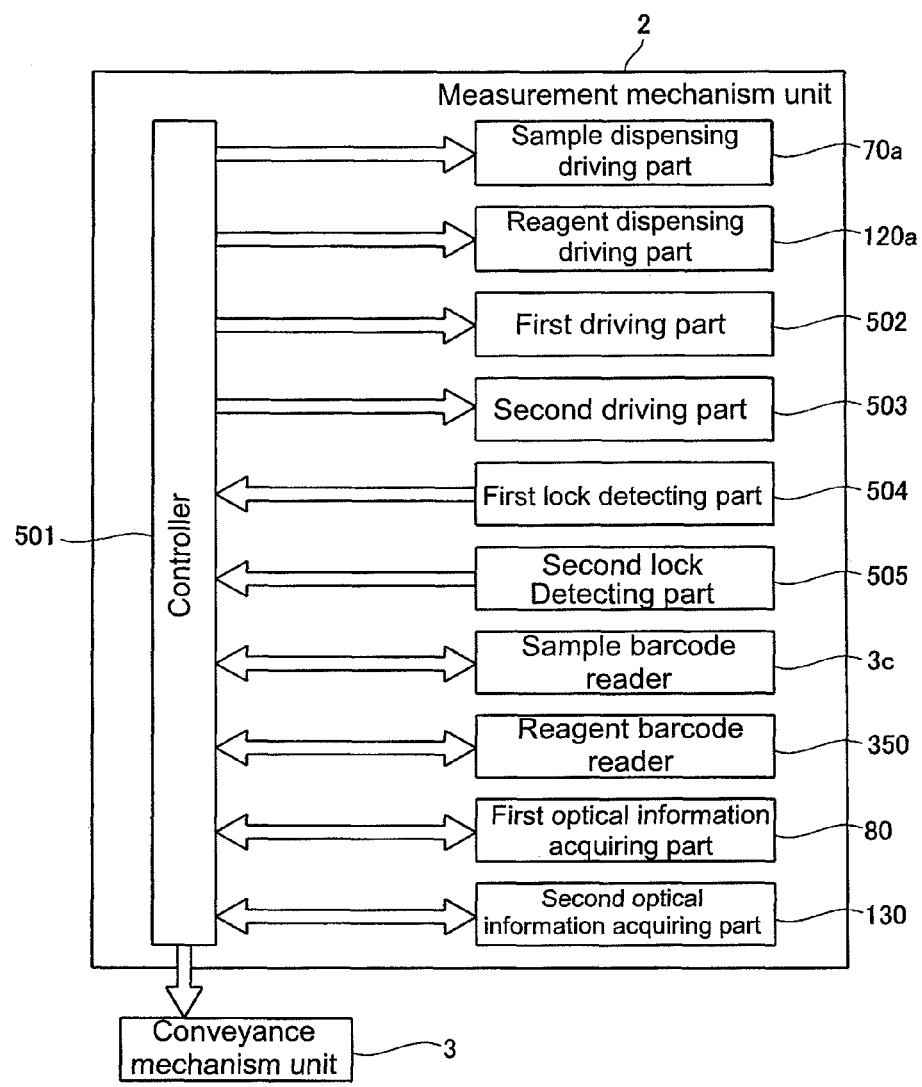
FIG. 20 is a block diagram of the sample analyzer according to one embodiment of the present invention.

As shown in FIG. 20, the measurement mechanism unit 2 includes a sample dispensing driving part 70a, a reagent dispensing driving part 120a, a first driving part 502, a second driving part 503, a first lock detecting part 504, a second lock detecting part 505, a reagent barcode reader 350, a sample barcode reader 3c, a first optical information acquiring part 80, a second optical information acquiring part 130, and a controller 501 electrically connected to the conveyance mechanism unit 3 and the like.

The sample dispensing driving part 70a includes a stepping motor 70b having a function of rotating a sample dispensing arm 70 (see FIGS. 3 and 5), to be hereinafter described, up and down, a drive circuit (not shown) for driving the stepping motor 70b, and a pump (not shown) for aspirating and dispensing the sample.

The reagent dispensing driving part 120a includes a stepping motor 120b having a function of rotating a reagent dispensing arm 120 (see FIGS. 3 and 5), to be hereinafter described, up and down, a drive circuit (not shown) for driving the stepping motor 120b, and a pump (not shown) for aspirating and dispensing the reagent.

The first driving part 502 includes a first stepping motor (not shown) having a function of rotating a first reagent table 11 (see FIG. 5), and a drive circuit (not shown) for driving the first stepping motor. The first reagent table 11 rotates by the amount corresponding to the number of pulses of the drive pulse signal provided from the controller 501 to the first driving part 502, and then stops.

Similarly, the second driving part 503 includes a second stepping motor (not shown) having a function of rotating a second reagent table 12 (see FIG. 5), and a drive circuit (not shown) for driving the second stepping motor. The second reagent table 12 rotates by the amount corresponding to the number of pulses of the drive pulse signal provided from the controller 501 to the second driving part 503, and then stops.

The controller 501 counts the number of pulses of the provided drive pulse signal to determine the rotatable movement amount of each reagent table 11, 12 from the origin position of the first reagent table 11 and the second reagent table 12 and control the rotatable movement of each reagent table 11, 12.

The first lock detecting part 504 has a function of detecting the lock state of the first lid 30 (see FIG. 3), and transmits the lock signal to the controller 501 when locked.

Similarly, the second lock detecting part 505 has a function of detecting the lock state of the second lid 40 (see FIG. 3), and transmits the lock signal to the controller 501 when locked.

Figure 4:
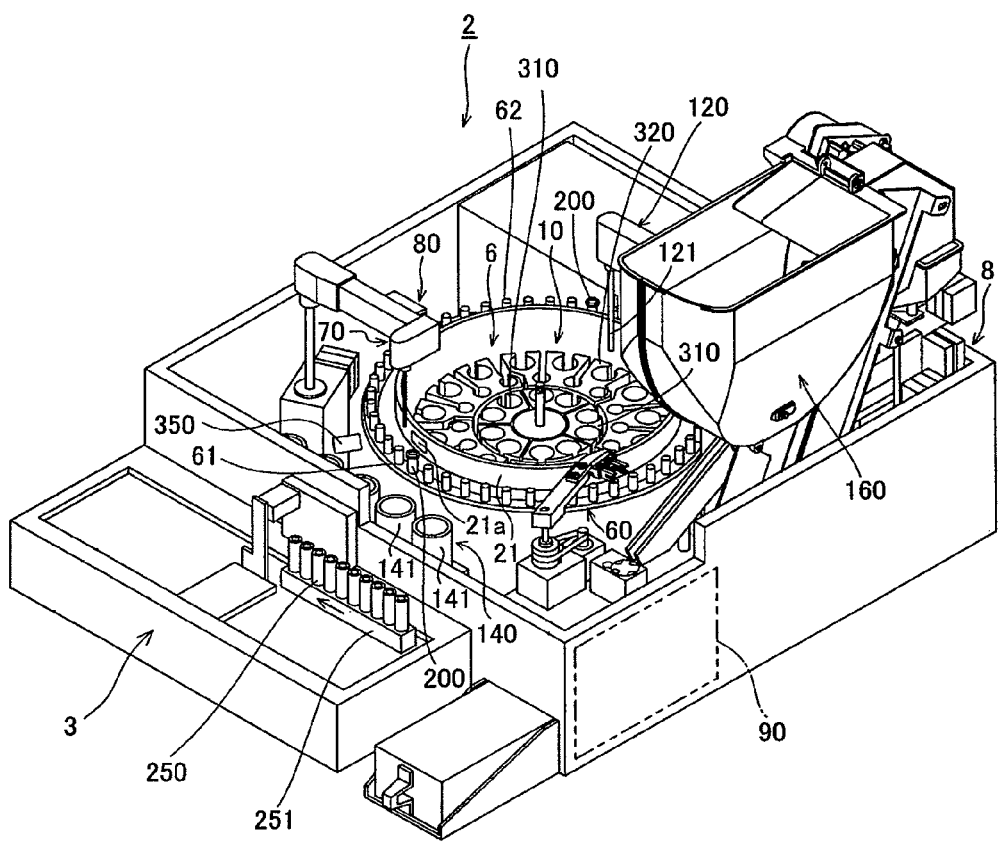
FIG. 4 is a perspective view showing the interior of the measurement mechanism unit and a reagent storing part of the sample analyzer according to one embodiment of the present invention.

The reagent barcode reader 350 has a function of reading each barcode of the first reagent table 11 and the second reagent table 12, and is arranged with a predetermined distance from the reagent storing part 6 near the side surface 21 of the reagent storing part 6 (see FIGS. 3 to 5). The reagent barcode reader 350 can transmit and receive data with the controller 501, and includes a drive circuit (not shown) for ON/OFF controlling the reagent barcode reader 350. The position of the reagent barcode reader 350 is always fixed.

The sample barcode reader 3c has a function of reading the barcode attached to a test tube 250 placed in the rack 251 conveyed by the conveyance mechanism unit 3, and is arranged to face the rack 251 conveyed by the conveyance mechanism unit 3 in the vicinity of the aspirating position 2a of the measurement mechanism unit 2 (see FIGS. 3 to 5). The sample barcode reader 3c can transmit and receive data with the controller 501, and includes a drive circuit (not shown) for ON/OFF controlling the sample barcode reader 3c. The position of the sample barcode reader 3c is always fixed.

Figure 21:
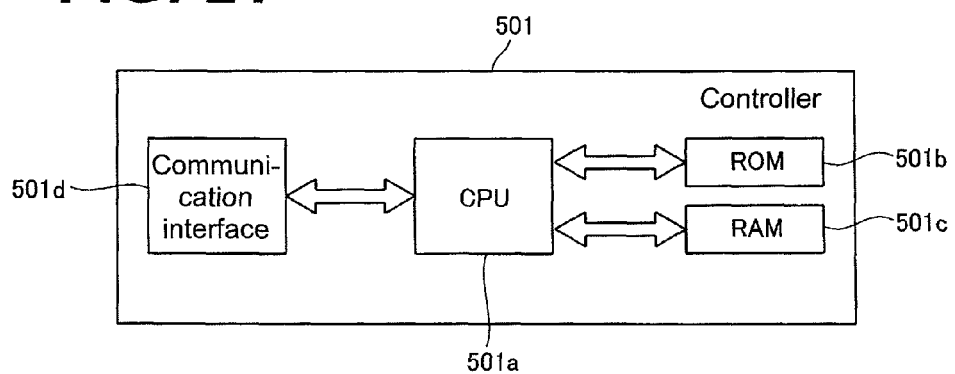
FIG. 21 is a block diagram of a controller of a measurement mechanism unit of the sample analyzer according to one embodiment of the present invention.

As shown in FIG. 21, the controller 501 is mainly configured by a CPU 501a, a ROM 501b, a RAM 501c, and a communication interface 501d.

The CPU 501a can execute the computer program stored in the ROM 501b and the computer program read out to the RAM 501c. The ROM 501b stores the computer program to be executed by the CPU 501a, the data used for the execution of the computer program, and the like. The RAM 501c is used to read out the computer program stored in the ROM 501b. The RAM 501c is used as a work region of the CPU 501a when executing the computer programs.

The communication interface 501d is connected to the control device 4, and has a function of transmitting optical information of the sample to the control device 4 and receiving signals from the controller 4a of the control device 4. The communication interface 501d also has a function of transmitting a command from the CPU 501a for driving each part of the conveyance mechanism unit 3 and the measurement mechanism unit 2.

As shown in FIG. 3, the measurement mechanism unit 2 includes the reagent storing part 6 for storing reagent, and the reagent replacing part 7 for replacing or adding the reagent.

The reagent storing part 6 is arranged to refrigerate the reagent container 300 accommodating the reagent to be added to the sample in the cuvette 200 at a low temperature (about 10° C.), and to convey the reagent container 300 in the rotating direction. The reagent is suppressed from alteration by being refrigerated at low temperature. As shown in FIGS. 3 to 5, the reagent storing part 6 includes a reagent conveying portion 10 (see FIGS. 4 and 5) for holding the reagent and rotatably conveying the same, and an outer wall portion 20

(see FIG. 3) arranged to cover the periphery and the upper side of the reagent conveying portion 10. The reagent conveying portion 10 holding the reagent is arranged in a refrigeration region formed by the outer wall portion 20, and the first lid 30 and the second lid 40 of the reagent replacing part 7, to be described below.

As shown in FIG. 5, the reagent conveying portion 10 includes the first reagent table 11 of circular shape, and, in the outer side of first reagent table 11 of circular shape, the second reagent table 12 of circular ring shape arranged concentrically with respect to the first reagent table 11. The first reagent table 11 and the second reagent table 12 are respectively configured such that the first reagent container rack 310 and the second reagent container rack 320 holding the reagent container 300 can be removably arranged. The outer wall portion 20 is configured by the side surface 21 (see FIG. 4), the upper surface 22 (see FIG. 3) fixed to the side surface 21, and the removable lid 23 (see FIG. 3). The reagent barcode reader 350 is arranged with a predetermined distance with the reagent storing part 6 near the side surface 21 (see FIG. 4) of the reagent storing part 6.

The first reagent table 11 and the second reagent table 12 are respectively configured so as to be rotatable in both the clockwise direction and the counterclockwise direction, each table being rotatable independent from each other. The first reagent container rack 310 and the second reagent container rack 320 for holding the reagent container 300 accommodating the reagent are respectively conveyed in the rotating direction by the first reagent table 11 and the second reagent table 12.

A heat insulating material (not shown) is attached to the side surface 21 of the outer wall portion 20, and is configured to prevent the cold air in the reagent storing part 6 (refrigeration region) from escaping. As shown in FIG. 4, an openable/closable shutter 21a is arranged at a position facing the reagent barcode reader 350 of the side surface 21 of the outer wall portion 20. The shutter 21a is configured to open only when reading the barcode of the reagent container 300, the first reagent container rack 310, and the second reagent container rack 320 by the reagent barcode reader 350. Thus, the cold air in the reagent storing part 6 (refrigeration region) is suppressed from escaping outside.

As shown in FIG. 3, the upper surface 22 of the outer wall portion 20 includes three holes 22a, 22b, and 22c. The reagent stored in the reagent storing part 6 is aspirated by the reagent dispensing arm 120 through the three holes 22a, 22b, and 22c.

A semicircular opening forms in the reagent storing part 6 (refrigeration region) by detaching the lid 23 with the first lid 30 and the second lid 40. When starting the measurement in the sample analyzer 1 through the opening, the first reagent container rack 310 and the second reagent container rack 320 are arranged in the reagent storing part 6.

Figure 16:
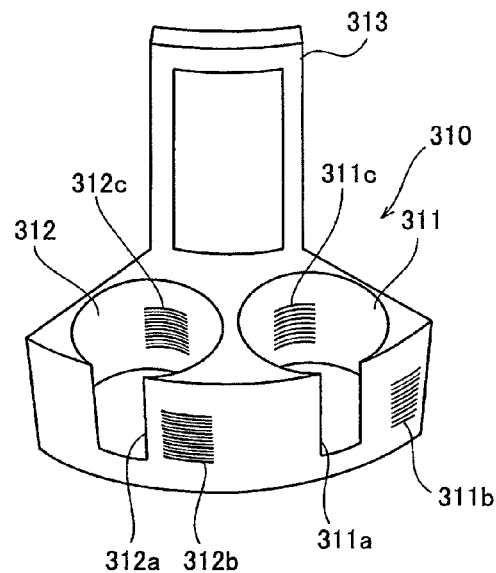
FIG. 16 is a perspective view showing a first reagent container rack used in the sample analyzer according to one embodiment of the present invention.
Figure 18:
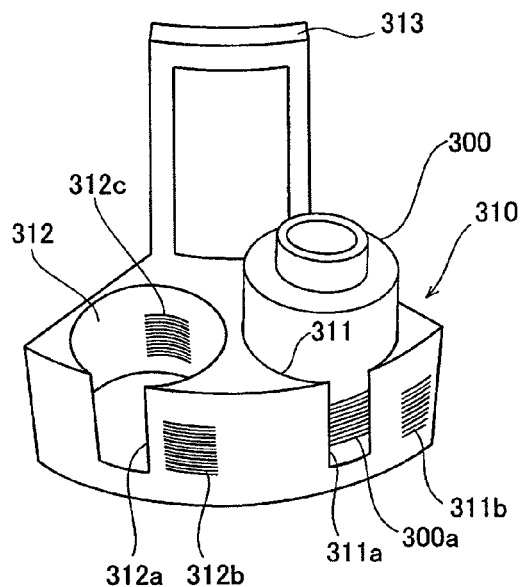
FIG. 18 is a perspective view showing a state in which the reagent container is held in the first reagent container rack shown in FIG. 16.

As shown in FIG. 5, five first reagent container racks 310 can be arranged in the first reagent table 11. The reagent container 300 is arranged in a circular ring shape in the five first reagent container racks 310. As shown in FIGS. 16 and 18, the first reagent container rack 310 includes two holders 311 and 312 for holding the reagent container 300, cutouts 311a and 312a respectively formed at the front surface side of the holders 311 and 312, and one grip 313 arranged projecting to the upper side. As shown in FIG. 16, the holders 311 and 312 are formed to a circular shape in plan view, and can hold the reagent container 300 by inserting a cylindrical reagent container 300. The barcodes 311b and 312b are respectively provided on the front surface side of the outer side surfaces of the holders 311 and 312, and barcodes 311c and 312c are respectively provided on the inner side surfaces of the holders 311 and 312.

Two holders 311 and 312 can hold, one at a time, a plurality of reagent containers 300 accommodating various kinds of reagents to be added when preparing the measurement sample from the specimen. In other words, a maximum of ten (2×5=10) reagent containers 300 can be arranged in the first reagent table 11. Each cutout 311a and 312a is provided to read the barcodes 311c and 312c with the reagent barcode reader 350 (see FIG. 5). The grip 313 is gripped when taking out the first reagent container rack 310 from the reagent storing part 6.

Each barcode 311b and 312b includes positional information (holder number) for identifying the positions of the holders 311 and 312. The barcodes 311c and 312c include information (no reagent container information) indicating that the reagent container 300 held by the holders 311 and 312 does not exist. The barcode 300a of the reagent container 300 includes information for specifying the detailed information (information such as reagent name, kind of reagent container, lot number, and expiration date of reagent) of the reagent accommodated in the reagent container 300.

For instance, if the reagent container 300 is held by the holder 311, the barcode 311c is not read and the barcode 300a of the reagent container 300 is read. In other words, if the barcode 300a is read after reading the barcode 311b is read by the reagent barcode reader 350, the controller 4a recognizes that the reagent having the reagent information by the barcode 300a is held by the holder 311. In the reagent arrangement displaying region 420 of the reagent management screen 410, the first reagent mark 421 is displayed at the position corresponding to the holder 311. If the barcode 311c is read after the barcode 311b is read by the reagent barcode reader 350, the controller 4a recognizes that the reagent container 300 held by the holder 311 does not exist. In the reagent arrangement displaying region 420 of the reagent management screen 410, a no-reagent arrangement mark 427 is displayed at the position corresponding to the holder 311. If neither the barcode 300a nor the barcode 311c is not read after the barcode 311b is read by the reagent barcode reader 350 (when the reagent container 300 is facing the side), the controller 4a recognizes the reading error and displays the barcode reading error mark E indicating that the reading failed in the display 4b. If the first reagent container rack itself is not arranged in the first reagent table 11, the reagent barcode 350 does not read the barcodes 311b, 312b, 311c, 312c of the first reagent container rack 310 and the barcode 300a of the reagent container 300. Thus, in the reagent arrangement displaying region 420 of the reagent management screen 410, a no-rack arrangement mark 426 is displayed on the first rack mark 424 corresponding to the portion not arranged with the first reagent container rack 310.

Figure 17:
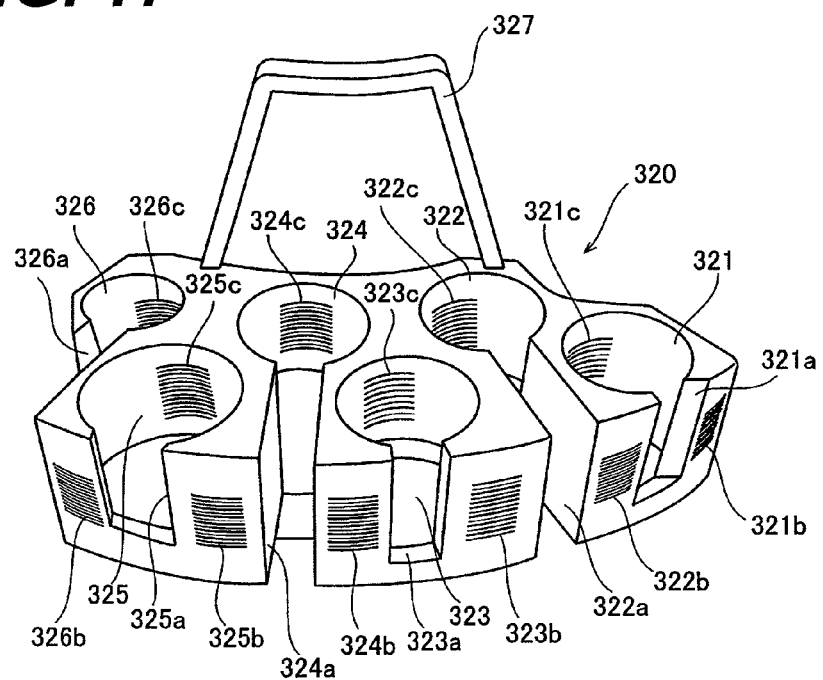
FIG. 17 is a perspective view showing a second reagent container rack used in the sample analyzer according to one embodiment of the present invention.
Figure 19:
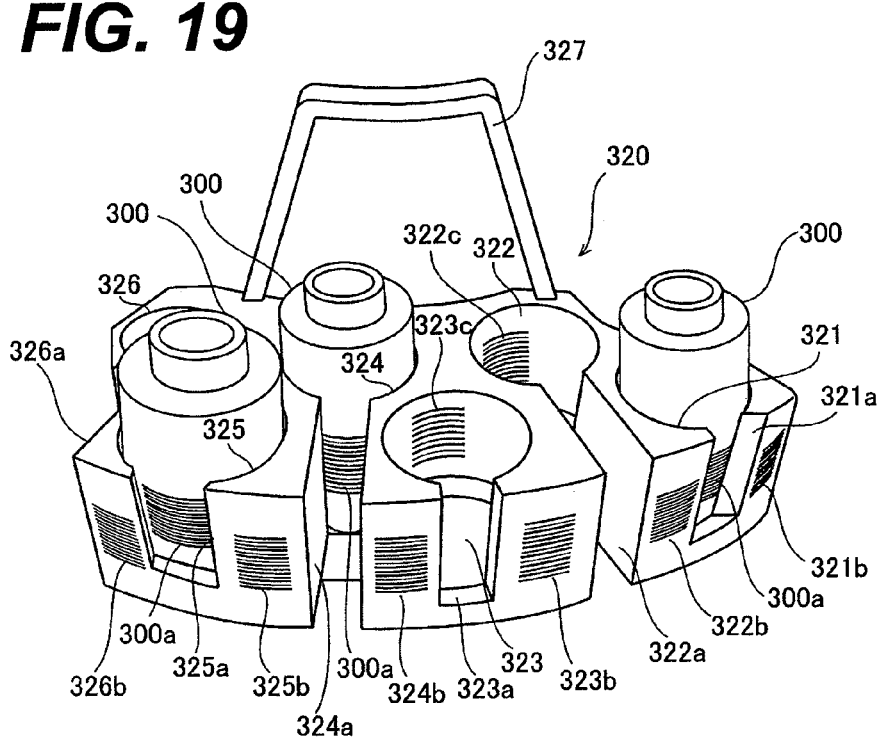
FIG. 19 is a perspective view showing a state in which the reagent container is held in the second reagent container rack shown in FIG. 17.

As shown in FIG. 5, five second reagent container racks 320 are arranged in the second reagent table 12. The reagent container 300 is arranged in a circular ring shape in the five reagent container racks 320. One location of the gap of the five locations of the second reagent container rack 320 adjacent to each other has an interval larger than the interval of the gap of other four locations. The barcodes 311b and 312b of the first reagent container rack 310 arranged in the first reagent table 11 positioned on the inner side of the second reagent table 12 and the barcode 300a of the reagent container 300 held by the first reagent container rack 310 are read by the reagent barcode reader 350 positioned on the outside of the reagent storing part 6 through the gap 12a having a large interval. As shown in FIGS. 17 and 19, the second reagent container rack 320 includes six holders 321 to 326 for holding the reagent container 300, cutouts 321a to 326a formed on the front surface side of the holders 321 to 326, and one grip 327 arranged projecting to the upper side. The holders 321 to 326 of the second reagent container rack 320 are formed to a circular shape in plan view, similar to the first reagent container rack 310, and can hold the reagent container 300 by inserting the cylindrical reagent container 300.

The barcodes 321b and 322b are formed on both sides of the cutout 321a on the front row side. Similarly, the barcodes 323b and 324b, and the barcodes 325b and 326b are formed on both sides of the cutout 323a and both sides of the cutout 325a. The barcodes 321c to 326c are formed on the inner side surfaces of the holders 321 to 326.

Each barcode 321b to 326b includes positional information (holder number) for identifying the position of the holder 321 to 326. The barcodes 321c and 326c include information (no-reagent container information) indicating that the reagent container 300 held by the holder 321 to 326 does not exist.

The reagent information or the no-reagent container information read by the reagent barcode reader 350 are stored in the reagent information database 36 of the hard disc 401d of the controller 4a in correspondence with the positional information (holder number). The information stored in the reagent information database 36 of the hard disc 401d is reflected on the reagent management screen 410 of the display 4b by the controller 4a of the control device 4.

The barcodes 311b, 312b, and 321b to 326b show the values of four digits. The first digit takes the value of "A" or "B", wherein "A" indicates that the reagent container 300 is arranged on the second reagent table 12, and "B" indicates that the reagent container 300 is arranged on the first reagent table 11. The second digit takes a value of "1" to "5", wherein "1" to "3" show three kinds of shapes of the second reagent container rack 320, and "4" and "5" show two kinds of shapes of the first reagent container rack 310. The third digit takes a value of "0" to "9", and indicates the number of the first reagent container rack 310 or the second reagent container rack 320. The fourth digit takes a value of "1" or "2" in the barcodes 311b and 312b of the first reagent container rack 310, wherein "1" and "2" show the holders 311 and 312, respectively. The fourth digit takes a value of "1" to "6" in the barcodes 321b to 326b of the second reagent container rack 320, wherein "1" and "6" show the holders 321 to 326. The value of the barcode (barcode 311b, 312b, and 321b to 326b) is reflected on the position displaying portion 421a of the first reagent mark 421 of the reagent management screen 410, the position displaying portion 422a of the second reagent mark 422, or the position displaying portion 427a of the no-reagent arrangement mark 427, as shown in FIG. 7. If the value of the barcode is "A11-6", the container can be arranged on the second reagent table 12, it is the rack (second reagent container rack 320) corresponding to "1" of the three kinds, and is the sixth holder (holder 326) of the second reagent container rack 320 of the rack number 1. In other words, the first three digits of the values of the four digits specify the reagent container rack, and the last one digit specifies the position of the reagent in the relevant reagent container rack.

The reagent name of the detailed information is reflected on the reagent name displaying portions 421b and 422b of the first reagent mark 421 and the second reagent mark 422 of the reagent management screen 410. The no-reagent container information is reflected on the no-reagent arrangement mark 427. In other words, as shown in FIG. 7, the reagent name is displayed on the reagent name displaying portion 421b or 422b when the reagent is arranged, and no display is made on the reagent name displaying portion 421b or 422b when the reagent is not arranged. For instance, in FIG. 7, the reagent name "CaC12" is arranged at the reagent position "A12-5" and no reagent is arranged at the reagent position "A14-2".

As shown in FIGS. 1 and 2, the reagent replacing part 7 is arranged near the central part of the sample analyzer 1. In the present embodiment, the reagent replacing part 7 includes the first lid 30 and the second lid 40, which are detachable, with lock mechanisms 31 and 41, respectively, and a notifying portion 50 for notifying the conveying state of the first reagent table 11 and the second reagent table 12 to the user, as shown in FIG. 3.

The first lid 30 is configured to be detachable when replacing the reagent container 300 arranged on the first reagent table 11 (first reagent container rack 310). The lock mechanism 31 of the first lid 30 is locked to prevent the first lid 30 from detaching in time of normal use or after replacement or addition of the reagent is terminated, and is provided to have the controller 4a recognize that the replacement or the addition of the reagent at the first reagent table 11 is terminated.

The second lid 40 is configured to be detachable when replacing the reagent container 300 arranged on the second reagent table 12 (second reagent container rack 320). The lock mechanism 41 of the second lid 40 is locked to prevent the second lid 40 from detaching in time of normal use or after replacement of the reagent is terminated, and is provided to have the controller 4a recognize that the replacement or the addition of the reagent at the second reagent table 12 is terminated.

The notifying portion 50 includes two LED indicators 51 and 52. As shown in FIGS. 1 and 3, the two LED indicators 51 and 52 are arranged near the second lid 40, and are visible by the user from outside the sample analyzer 1. The LED indicators 51 and 52 can emit light in blue or red.

The LED indicator 51 has a function of notifying the user that the first reagent container rack 310 corresponding to the reagent of the first reagent table 11 specified on the reagent management screen 410 by the user moved to a retrieving position (lower side of first lid 30) where the reagent can be replaced.

The LED indicator 52 has a function of notifying the user that the second reagent container rack 320 corresponding to the reagent of the second reagent table 12 specified on the reagent management screen 410 by the user moved to a retrieving position (lower side of second lid 40) where the reagent can be replaced.

The user locks the first lid 30 or the second lid 40 after the replacement or the addition of the reagent is terminated, wherein the sample analyzer 1 is configured such that the reading of the barcode 300a of all the reagent containers 300 held by the first reagent container rack 310 or the second reagent container rack 320 holding the replaced reagent which is automatically performed. Thus, when one reagent is specified and the replacement of the reagent is instructed, the arrangement of the reagent after the replacement is correctly reflected on the reagent management screen 410 even when the reagent other than the specified reagent included in the same first reagent container rack 310 or the second reagent container rack 320 is replaced in addition to the specified reagent.

As shown in FIGS. 3 to 5, the measurement mechanism unit 2 includes a cuvette conveying part 60, a sample dispensing arm 70, a first optical information acquiring part 80, a lamp unit 90, a heating part 100, a cuvette transfer part 110, a reagent dispensing arm 120, a second optical information acquiring part 130, an emergency sample setting portion 140, a fluid part 150, and a cuvette supply mechanism section 160.

The cuvette conveying part 60 has a function of conveying the cuvette 200 to each portion of the sample analyzer 1. The cuvette conveying part 60 includes a cuvette conveying table 61 of circular ring shape arranged on the outer side of the second reagent table 12 of circular ring shape, and a plurality of cylindrical cuvette holders 62 arranged with a predetermined spacing along the circumferential direction on the cuvette conveying table 61. The cuvette holder 62 is arranged to hold the cuvette 200 one at a time.

The sample dispensing arm 70 has a function of aspirating the sample accommodated in the test tube 250 conveyed to the aspirating position 2a by the conveyance mechanism unit 3, and dispensing the aspirated sample to the cuvette 200 held at the cuvette holder 62 of the cuvette conveying table 61. As shown in FIG. 4, the sample dispensing arm 70 is configured to move a pipette (not shown) in the up and down direction by a pulse control of the stepping motor (not shown). A sensor (not shown) for detecting the liquid level of the sample is arranged at the distal end of the pipette of the sample dispensing arm 70. Thus, when measuring the remaining amount of the reagent, the liquid level of the reagent, which remaining amount is to be measured, accommodated in the reagent container 300 is detected by the sensor. Thus, the height of the liquid level of the reagent in the reagent container 300 can be calculated by the number of pulses and the movement amount for one pulse for until the liquid level is detected.

The first optical information acquiring part 80 is configured to acquire optical information from the sample to measure the presence and the concentration of the interfering substance (milky fluid (fat), hemoglobin, and bilirubin) in the sample to which the reagent is added.

The acquisition of the optical information of the sample by the first optical information acquiring part 80 is performed before the optical measurement of the sample by the second optical information acquiring part 130. The first optical information acquiring part 80 acquires the optical information (information by transmitted light of the sample) from the sample in the cuvette 200 held at the cuvette holder 62 of the cuvette conveying table 61.

The first optical information acquiring part 80 is electrically connected to the controller 4a of the control device 4, and transmits the data (optical information) acquired by the first optical information acquiring part 80 to the controller 4a of the control device 4.

As shown in FIGS. 3 to 5, the reagent dispensing arm 120 is arranged to mix the reagent to the sample in the cuvette 200 by dispensing the reagent in the reagent container 300 mounted on the reagent storing part 6 to the cuvette 200. The reagent is added to the sample, which optical measurement by the first optical information acquiring part 80 is finished, to prepare the measurement sample.

The reagent dispensing arm 120 is configured to move the pipette 121 in the up and down direction by the pulse control of the stepping motor (not shown) when performing the dispensing operation. A sensor (not shown) for detecting the liquid level of the reagent when aspirating the reagent from the reagent container 300 is arranged at the distal end of the pipette 121 of the reagent dispensing arm 120. The height of the liquid level of the reagent in the reagent container 300 can be calculated by the number of pulses and the movement amount for one pulse for until the liquid level of the reagent is detected. The procedure for calculating the height of the liquid level of the reagent will be described in detail hereinafter.

The second optical information acquiring part 130 has a function of measuring optical information from the measurement sample. As shown in FIG. 5, the second optical information acquiring part 130 is configured by a measurement mounting portion 131 and a detecting portion 132 arranged on the lower side of the measurement mounting portion 131.

The second optical information acquiring part 130 is electrically connected to the controller 4a of the control device 4, and transmits the acquired data (optical information) to the controller 4a of the control device 4. Thus, in the control device 4, the data (optical information) transmitted from the second optical information acquiring part 130 is analyzed and displayed on the display 4b.

As shown in FIGS. 3 to 5, the emergency sample setting portion 140 is arranged to perform a sample analyzing process on the emergency sample. The emergency sample setting portion 140 is configured to cut in the emergency sample when the sample analyzing process on the sample supplied from the conveyance mechanism unit 3 is being performed. The emergency sample setting portion 140 is slidable in the X direction, and includes five holders 141 for holding container (not shown) accommodating the diluting fluid and the cleaning fluid. The container (not shown) accommodating the diluting fluid and the cleaning fluid is attached with a barcode (not shown). The barcode of the diluting fluid and the cleaning fluid is read by the barcode reader 351 while the emergency sample setting portion 140 is being sled in the X direction. The kind, arrangement, and the like of the diluting fluid and the cleaning fluid are displayed as the diluting/cleaning fluid mark 423 of the reagent management screen 410. As shown in FIGS. 1 and 2, a lid 1c is arranged on the front surface side of the replacing part 7 of the sample analyzer 1. The replacement or the addition of the container (not shown) accommodating the diluting fluid and the cleaning fluid is performed through the lid 1c.

The cuvette supply mechanism section 160 is configured such that a plurality of cuvettes 200 randomly inserted to the hopper 161a by the user is sequentially supplied to the cuvette conveying part 60.

The analyzing operation of the sample of the sample analyzer 1 will be described in detail with reference to FIGS. 4 and 5. Here, the operation in the measurement using the coagulation time method will be described herein.

First, the initial setting of the sample analyzer 1 is performed by turning ON the powers of the measurement mechanism unit 2 and the control device 4 of the sample analyzer 1 shown in FIG. 4. The operation for returning the mechanism for moving the cuvette 200 and each dispensing arm (sample dispensing arm 70 and reagent dispensing arm 120) to the initial position, initialization of software stored in the controller 4a of the control device 4, and the like are performed.

The rack 251 mounted with the test tube 250 accommodating the sample is conveyed by the conveyance mechanism unit 3 shown in FIG. 5. The rack 251 is thereby conveyed to the position corresponding to the aspirating position 2a of the measurement mechanism unit 2.

A predetermined amount of sample is aspirated from the test tube 250 by the sample dispensing arm 70. The sample dispensing arm 70 is then moved to the upper side of the cuvette 200 held at the cuvette conveying table 61 of the cuvette conveying part 60. Thereafter, the sample is dispensed to the cuvette 200 by discharging the sample into the cuvette 200 of the cuvette conveying table 61 from the sample dispensing arm 70.

The cuvette conveying table 61 is rotated to convey the cuvette 200 dispensed with the sample to a position where measurement can be made by the first optical information acquiring part 80. The optical measurement on the sample is performed by the first optical information acquiring part 80, the optical information is acquired from the sample, and the optical information is transmitted to the controller 4a of the control device 4.

The reagent dispensing arm 120 is then driven to add the reagent in the reagent container 300 mounted on the reagent table (first reagent table 11 or second reagent table 12) to the sample in the cuvette 200. The measurement sample is then prepared.

The optical measurement is performed under a plurality of conditions with respect to the measurement sample in the cuvette 200 by the detecting portion 132 of the second optical information acquiring part 130, so that the optical information (second optical information) is acquired from the measurement sample.

The acquired second optical information is sequentially transmitted to the controller 4a of the control device 4.

After the analysis by the controller 4a of the control device 4 is terminated, the obtained analysis result is displayed on the display 4b of the control device 4. The analyzing operation of the sample of the sample analyzer 1 is then terminated.

Figure 22:
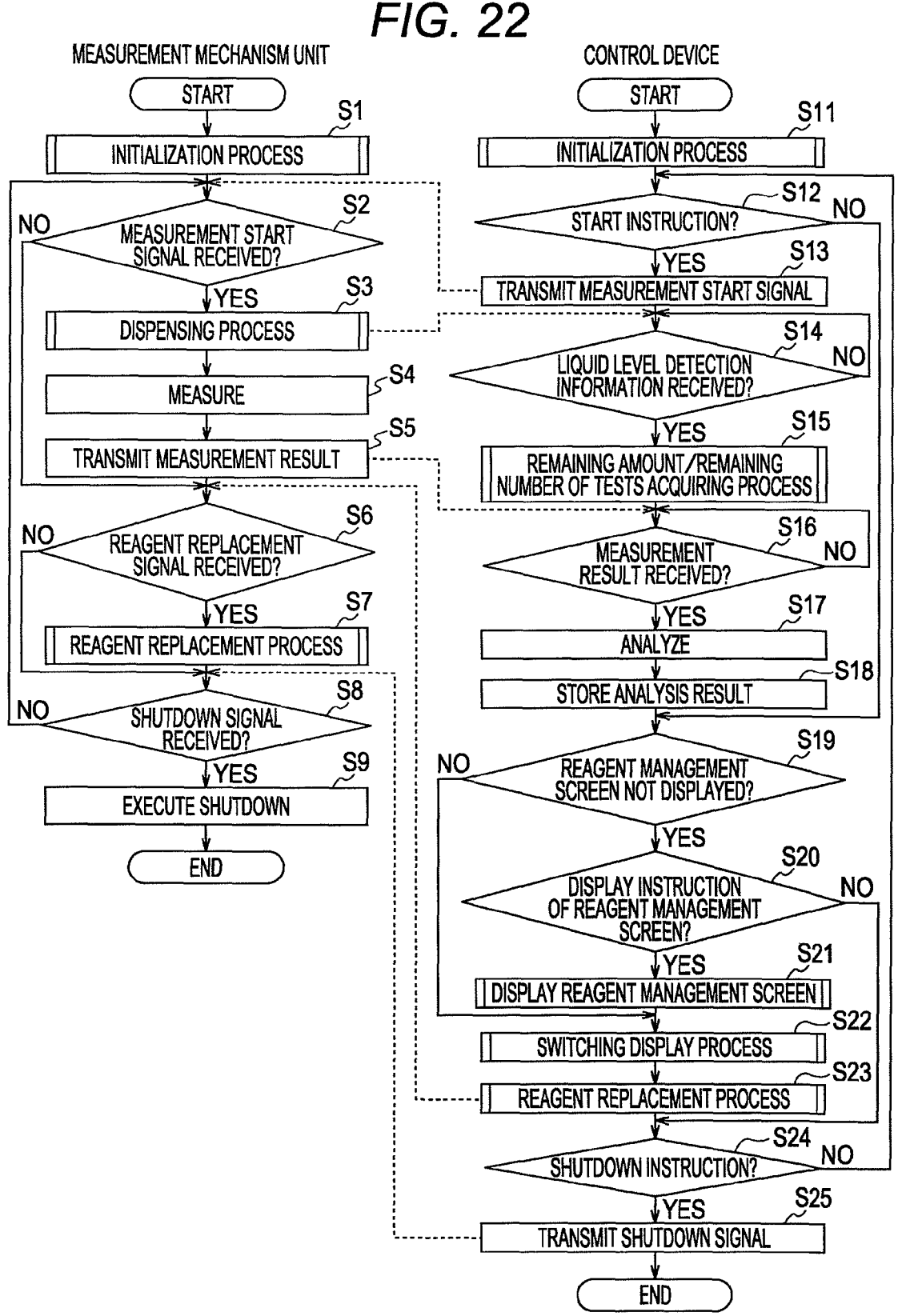
FIG. 22 is a flowchart for describing the measurement process of the control device and the measurement mechanism unit of the sample analyzer according to one embodiment of the present invention.

FIG. 22 is a flowchart for describing the measurement process flow of the control device and the measurement mechanism unit of the sample analyzer according to the present embodiment. The measurement process flow of the control device 4 and the measurement mechanism unit 2 of the sample analyzer 1 according to the present embodiment will be described with reference to FIGS. 7 and 22.

First, after setting all the reagents in the reagent storing part 6, the user turns ON the power (not shown) of the measurement mechanism 2, so that the initialization of the controller 501 (initialization of the program) is performed and the operation check of each portion of the measurement mechanism unit 2 are performed in step S1. When the user turns ON the power (not shown) of the control device 4, initialization of the controller 4a (initialization of the program) is performed in step S11. After the initialization of the controller 501 is completed, the controller 501 requests for an initialization complete signal indicating the completion of initialization of the controller 4a, and controls the reagent barcode 350 to read the barcode of all the reagents set in the reagent storing part 6 and the barcode of the reagent rack when receiving the initialization complete signal. The read barcode information is transmitted from the controller 501 to the controller 4a, and stored in the hard disc 401d of the controller 4a.

In step S12, a menu screen (not shown) is displayed on the display 4b, wherein when the user pushes the start button displayed on the menu screen, a measurement start signal is transmitted from the controller 4a to the controller 501 in step S13. If the start button is not pushed in step S12, the process proceeds to step S19.

In step S2, whether or not the measurement start signal is received is determined by the controller 501, wherein the process proceeds to step S3 if determined that the measurement start signal is received, and the process proceeds to step S6 if determined that the measurement start signal is not received.

In step S3, a process of dispensing the reagent to the sample dispensed to the cuvette 200 is performed, the liquid level is detected when aspirating the reagent to acquire the liquid level detection information, and the liquid level detection information is transmitted form the controller 501 to the controller 4a. In step S4, the sample dispensed with the reagent is measured by the first optical information acquiring part 80 and the second optical information acquiring part 130, and in step S5, the measurement result is transmitted from the controller 501 to the controller 4a.

In step S14, whether or not the liquid level detection information is received is determined by the controller 4a, wherein the process proceeds to step S15 if determined that the liquid level detection information is received, and the determination is repeated if determined that the liquid level detection information is not received. In step S15, the remaining amount/remaining number of tests acquiring process of the reagent is performed by the controller 4a. The remaining amount/remaining number of tests acquiring process will be hereinafter described, but is a process of calculating the reagent remaining amount based on the liquid level detection information, calculating the remaining number of tests based on the reagent remaining amount, and storing the reagent remaining amount and the remaining number of tests in the reagent information database 36 of the hard disc 401d.

In step S16, whether or not the measurement result is received is determined by the controller 4a, wherein the process proceeds to step S17 if determined that the measurement result is received, and the determination is repeated if the measurement result is not received. In step S17, the measurement result is analyzed by the controller 4a, and in step S18, the analysis result is stored in the hard disc 401d.

In step S19, whether or not the reagent management screen 410 is displayed on the display 4b is determined by the controller 4a, wherein the process proceeds to step S20 if determined that the reagent management screen 410 is not displayed on the display 4b, and the process proceeds to step S22 if determined that the reagent management screen 410 is displayed on the display 4b. In step S20, whether or not a display instruction of the reagent management screen 410 is made (whether or not reagent button (not shown) for displaying the reagent management screen 410 of the menu screen) is determined by the controller 4a, wherein the process proceeds to step s21 if the display instruction of the reagent management screen 410 is made, and the process proceeds to step S24 if the display instruction of the reagent management screen 410 is not made. In step S21, the reagent management screen 410 is displayed by the controller 4a. The reagent management screen 410 shown in FIG. 7 is thus displayed on the display 4b, and necessary information are reflected on the first reagent mark 421, the second reagent mark 422, the diluting/cleaning fluid mark 423, the selection accepting region 428, and the reagent detailed information displaying region 430 displayed on the reagent management screen 410. The display process of the reagent management screen 410 will be hereinafter described. In step S22, a switching display process in the reagent management screen 410 is executed by the controller 4a. The details of the switching display process in the reagent management screen 410 will be hereinafter described.

In step S23, a reagent replacement process is performed. The reagent replacement process will be hereinafter described in detail.

In step S24, whether or not the instruction of shutdown is made is determined (whether or not the shutdown button (not shown) is pushed from the menu screen) by the controller 4a, wherein the process proceeds to step S25 if determined that the instruction of the shutdown is made, and the process returns to step S12 if determined that the instruction of the shutdown is not made. In step S25, the shutdown signal is transmitted from the controller 4a to the controller 501, the shutdown of the control device 4 is performed, and the process is terminated.

In step S6, whether or not the reagent replacement signal is received is determined by the controller 501, wherein the process proceeds to step S7 if determined that the reagent replacement signal is received, and the process proceeds to step S8 if determined that the reagent replacement signal is not received. In step S7, the reagent replacement process is performed by the controller 501.

Whether or not the shutdown signal is received is determined in step S8, wherein the process proceeds to step S9 if determined that the shutdown signal is received, and the process returns to step S2 if determined that the shutdown signal is not received. In step S9, the shutdown of the measurement mechanism unit 2 is performed, and the process is terminated.

In the measurement process flow of the measurement mechanism unit 2, step S3, step S4, and step S7 are parallel processed. In the measurement process flow of the control device 4, step S15, step S17, step S22, and step S23 are parallel processed.

Figure 23:
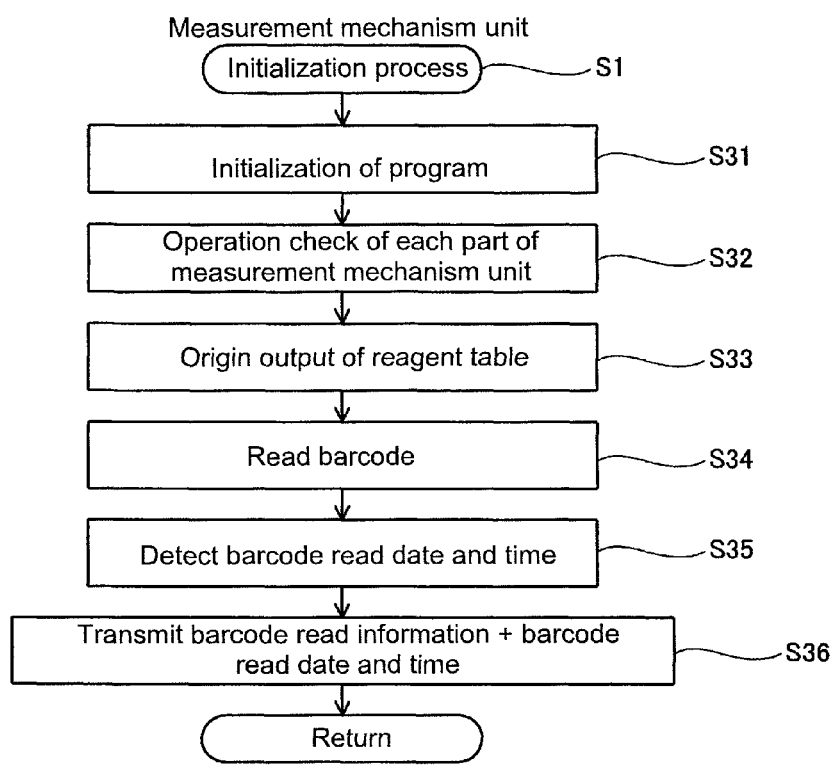
FIG. 23 is a flowchart for describing the initialization process of the measurement mechanism unit of the sample analyzer according to one embodiment of the present invention.

FIG. 23 is a flowchart for describing the details of the initialization process of the measurement mechanism unit executed in step S1 of the flowchart shown in FIG. 22. The initialization process of the measurement mechanism unit 2 of the sample analyzer 1 according to the present embodiment will be described with reference to FIGS. 15 to 18, and 23.

First, in step S31, the initialization of the program is performed. In step S32, the operation check of each part of the measurement mechanism unit 2 is performed. In step S33, the origin output of the reagent table (first reagent table 11 and second reagent table 12) is performed. Thereafter, the barcodes 311b, 311c, 312b, 312c, 321b to 326b and 321c to 326c of the rack (first reagent container rack 310 and second reagent container rack 320) and the barcode 300a (see FIGS. 15 to 18) of the reagent container 300 held in the rack are read in step S34, and the barcode read date and time are detected in step S35. Subsequently, the barcode read information and the barcode read date and time are transmitted to the control device 4 in step S36, whereby the initialization process of the measurement mechanism unit 2 is terminated.

Figure 24:
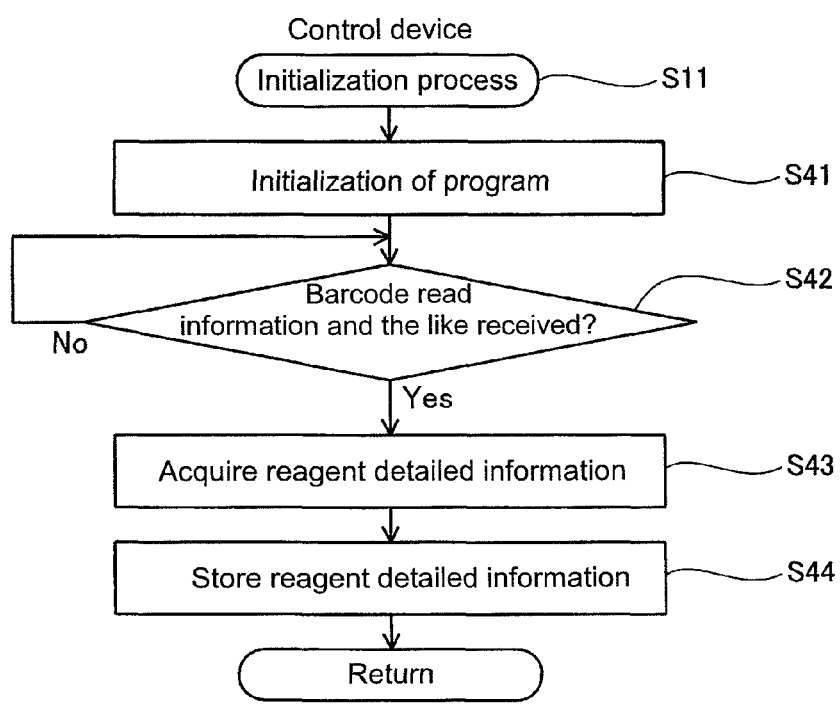
FIG. 24 is a flowchart for describing the initialization process of the control device of the sample analyzer according to one embodiment of the present invention.

FIG. 24 is a flowchart for describing the details of the initialization process of the control device executed in step S11 of the flowchart shown in FIG. 22. The initialization process of the control device 4 of the sample analyzer 1 according to the present embodiment will be described with reference to FIG. 24.

First, in step S41, the initialization of the program is performed. In step S42, whether or not the barcode read information and the barcode read date and time are received from the controller 501 of the measurement mechanism unit 2 is determined. If the barcode read information and the barcode read date and time are not received, such determination is repeated. If the barcode read information and the barcode read date and time are received, the reagent detailed information (holder number, reagent name, set date and set time of reagent, and the like) are acquired based on the barcode read information, the reagent table, and the barcode read date and time in step S43. The controller 4a specifies the set date and the set time the reagent is set by the barcode read date and time. In step S44, the reagent detailed information is stored in the reagent information database 36 of the hard disc 401d. Since the information of the reagent placed in the reagent storing part 6 before shutting down the sample analyzer 1 at the previous time is stored in the reagent information database 36, if the same reagent is set at the position same as the previous time, the controller 4a saves the reagent detailed information of the reagent information database 36 as is with respect to such reagents. With respect to the reagent set at a position different from the previous time, or the regent newly set for this time, the reagent detailed information of the corresponding record in the reagent information database 36 is deleted, and the reagent detailed information newly acquired for this time is stored in the reagent information database 36.

Thus, the reagent detailed information reflecting the arrangement state of the reagent in the reagent storing part 6 is stored in the reagent information database 36. The initialization process of the control device 4 is thereby terminated.

Figure 25:
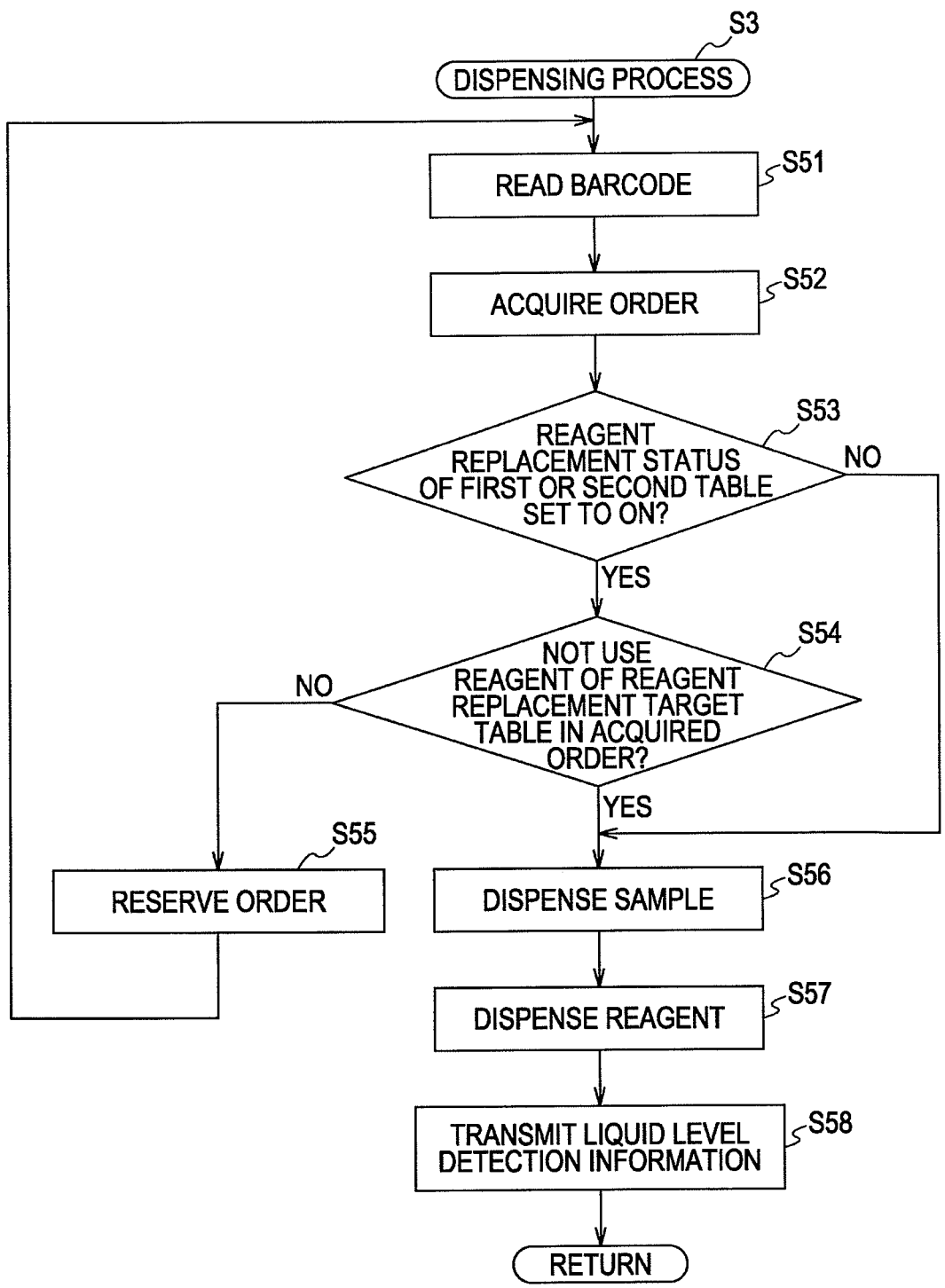
FIG. 25 is a flowchart for describing the dispensing process of the controller of the measurement mechanism unit of the sample analyzer according to one embodiment of the present invention.
Figure 26:
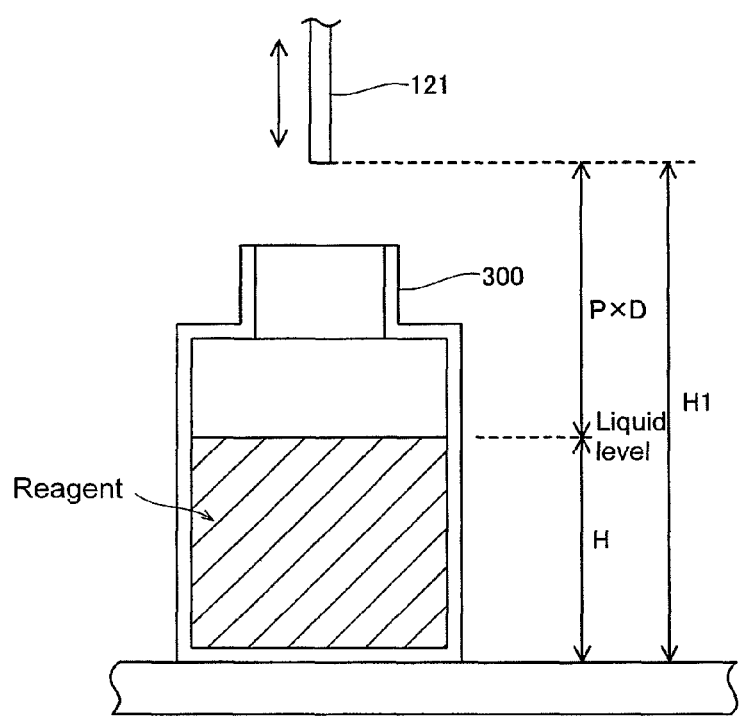
FIG. 26 is a conceptual view describing the calculation method of the reagent remaining amount.

FIG. 25 is a flowchart for describing the details of the dispensing process of the measurement mechanism unit executed in step S3 of the flowchart shown in FIG. 22. FIG. 26 is a view describing the calculation method of the reagent remaining amount. The dispensing process flow of the controller 501 of the measurement mechanism unit 2 of the sample analyzer 1 according to the present embodiment will be described with reference to FIGS. 3, 25 and 26.

First, the barcode attached to the test tube 250 accommodating the sample conveyed by the conveyance mechanism unit 3 is read by controlling the sample barcode reader 3c by the controller 501 in step S51 shown in FIG. 25. In step S52, the order is acquired based on the read barcode information by the controller 501, and the process proceeds to step S53. In step S53, whether or not the reagent replacement status of the first reagent table 11 or the second reagent table 12 is set to ON is determined by the controller 501. This process is performed by checking the status register incorporated in the drive circuit of the reagent replacement reagent table by the controller 501. If determined that the reagent replacement status of either the first reagent table 11 or the second reagent table 12 is set to ON in step S53, the process proceeds to step S54. If determined that neither reagent replacement status is not set to ON in step S53, the process proceeds to step S56. The order will be described below. The order is the information including the analyzing items corresponded to the information specifying the sample. The order is registered in a host computer (not shown) connected to the control device 4, or is stored through manual input by the user to the control device 4. After acquiring the barcode information of the sample, the control device 4 searches the relevant order from the order stored inside, or inquires the host computer with the sample ID as the key to acquire the order. The order acquired by the control device 4 is transmitted from the controller 4a of the control device 4 to the controller 501 of the measurement mechanism unit 2, and the controller 501 acquires the order.

In step S56, the sample dispensing driving part 70a is controlled according to the order by the controller 501, the sample stored in the test tube 250 conveyed by the conveyance mechanism unit 3 is aspirated and the aspirated sample is dispensed into the cuvette 200 held by the cuvette holder 62 of the cuvette conveying table 61 by the sample dispensing arm 70. In step S57, the reagent dispensing driving part 120a is controlled by the controller 501, and the reagent is aspirated through the holes 22a, 22b, or 22c (see FIG. 3) of the outer wall portion 20 of the reagent storing part 6 and the aspirated reagent is dispensed to the cuvette 200, which warming is completed, by the reagent dispensing arm 120. As shown in FIG. 26, in step S57, the pipette 121 of the reagent dispensing arm 120 is moved to the lower side from the initial position (height H1) for aspirating the reagent. The pipette 121 is driven by the stepping motor, and is moved by the movement distance D every time one pulse is input to the stepping motor. The liquid level of the reagent is detected by the sensor arranged at the distal end of the pipette 121. The number of pulses P, which is one liquid level detection information, of the case where the sensor detects the liquid level of the reagent is acquired. The acquired liquid level detection information is transmitted to the control device 4 by the controller 501 in step S58.

If determined that the reagent replacement status of either the first reagent table 11 and the second reagent table 12 is set to ON by the controller 501 in step S53, whether or not the analyzing item specified in the acquired order uses the reagent of the reagent replacement target table is determined. If determined that the analyzing item specified in the acquired order does not use the reagent of the reagent replacement target table in step S54, the process proceeds to steps S56, S57, and the processes described above are performed. If determined that the analyzing item specified in the acquired order use the reagent of the reagent replacement target table, the acquired order is reserved in step S55. The steps S51 to S55 are repeated until determined that the analyzing item specified in the acquired order does not use the reagent of the reagent replacement target table. In the reserved order, if determined that the analyzing item specified in the acquired order does not use the reagent of the reagent replacement target table, the processes of steps S56, S57, S58 are executed in order.

Figure 27:
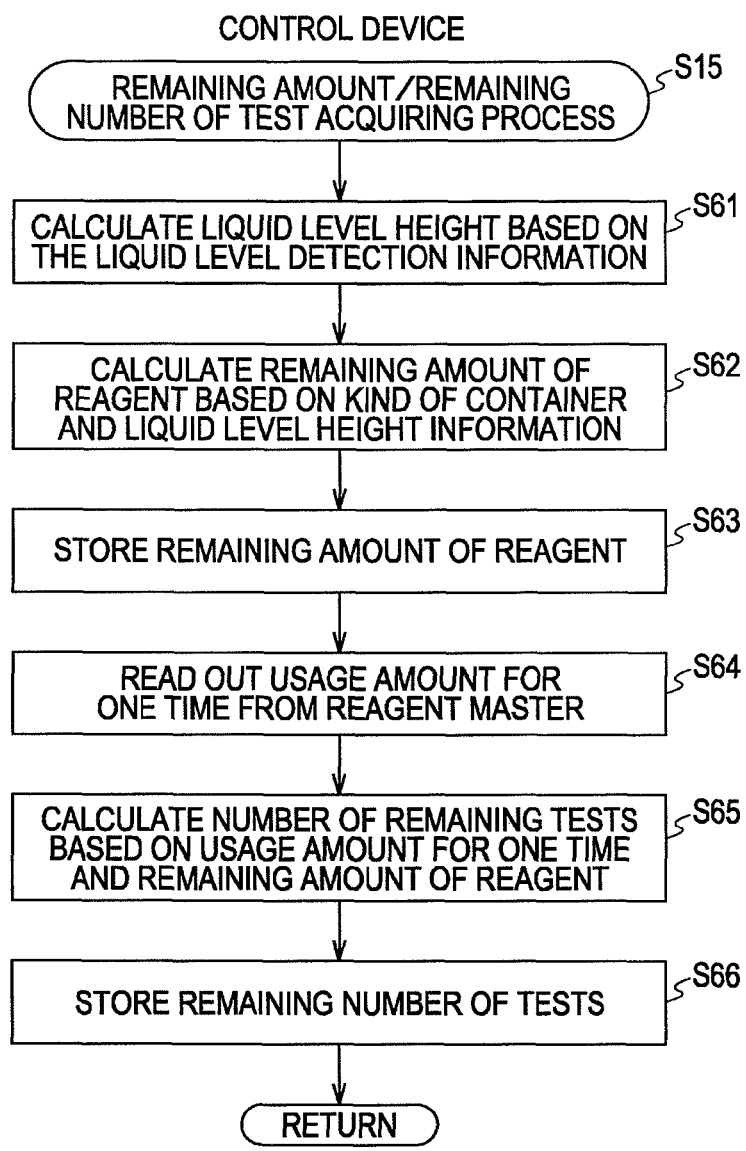
FIG. 27 is a flowchart for describing the reagent remaining amount/remaining number of tests acquiring process of the reagent by the control device of the sample analyzer according to one embodiment of the present invention.

FIG. 27 is a flowchart for describing the details of the reagent remaining amount/remaining number of tests acquiring process of the reagent by the control device executed in step S15 of the flowchart shown in FIG. 22. The process of calculating the remaining amount and the remaining number of tests of the reagent is then described with reference to FIGS. 26 and 27.

In step S61 shown in FIG. 27, the height of the liquid level is calculated based on the liquid level detection information by the controller 4a. The liquid level detection information includes the number of pulses P and the distance D of the case where the liquid level is detected. The container master is referenced by the controller 4a to specify the reagent container based on the container ID and acquire the inner surface area S in the horizontal direction of the specified reagent container. The reagent name is acquired based on the reagent ID with reference to the reagent master. The height H of the liquid level is obtained by the following equation (1) by the controller 4a, as shown in FIG. 26.

$$H(\text{height of liquid level}) = H1(\text{height of initial position}) - P(\text{number of pulses}) \times (\text{movement distance of one pulse}) \quad (1)$$

In step S62, the remaining amount T of the reagent is calculated by the following equation (2) by the controller 4a from the inner surface area S of the acquired reagent container and the acquired height H of the liquid level of the reagent.

$$T(\text{remaining amount}) = H(\text{height of liquid level}) \times S(\text{inner surface area of reagent container}) \quad (2)$$

In step S63, the controller 4a stores the calculated remaining amount T of the reagent in the field of "usable amount" of the corresponding record in the reagent information database 36 of the hard disc 401d. If the data of the reagent remaining amount is already stored in the field of "usable amount" of the record, the controller 4a deletes such data and newly stores the reagent remaining amount T calculated for this time.

In step S64, the usage amount of the reagent necessary for one measurement is read by the controller 4a by referencing the reagent master. In step S65, the remaining number of tests is calculated based on the usage amount of the reagent necessary for one measurement and the remaining amount T of the reagent stored in the reagent information database 36, and in step S66, the calculated remaining number of tests is stored in the field of "remaining number of tests" of the corresponding record in the reagent information database 36 of the hard disc 401d. If the data of the remaining number of tests is already stored in the field of "remaining number of tests", the controller 4a deletes the data and newly stores the remaining number of tests calculated for this time. Steps S61 to S66 are repeated every time the measurement is performed.

Figure 31:
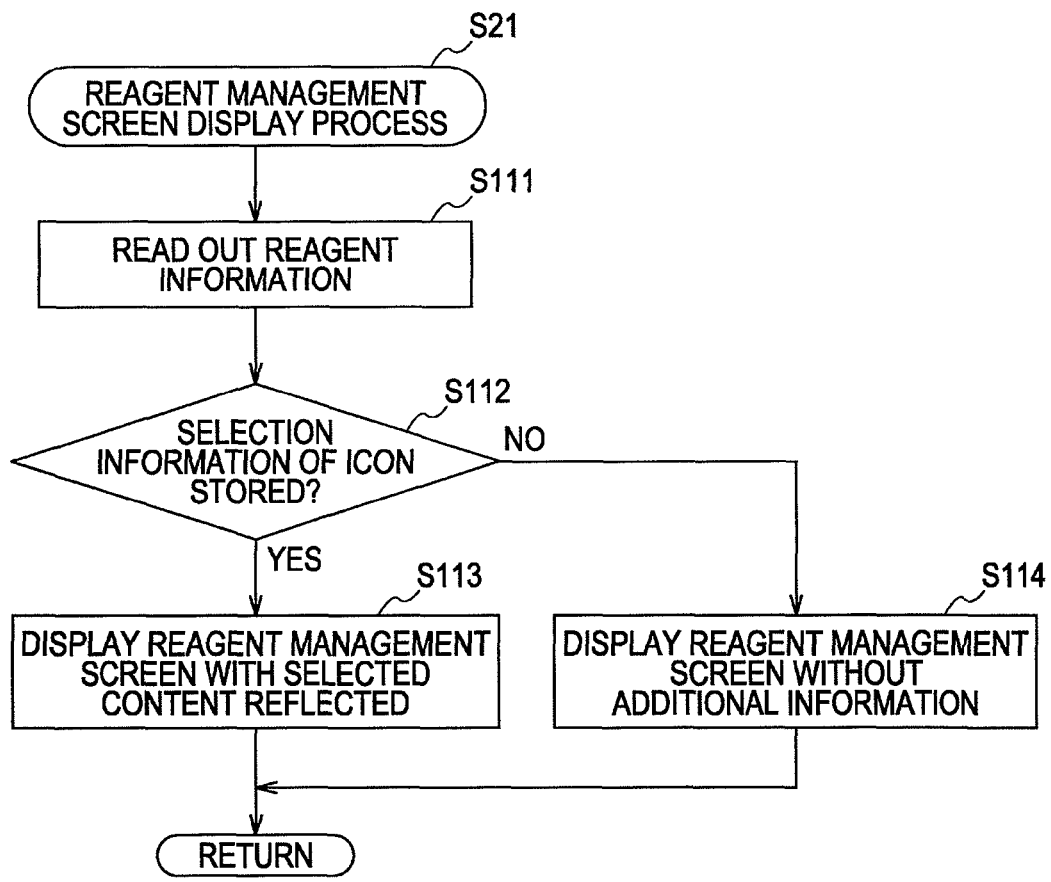
FIG. 31 is a flowchart for describing the display process of the reagent management screen of the sample analyzer according to one embodiment of the present invention.

FIG. 31 is a flowchart for describing the display process of the reagent management screen of the control device executed in step S21 of the flowchart shown in FIG. 22. The display process of the reagent management screen will be described below with reference to FIGS. 22 and 31.

As shown in FIG. 31, first all the reagent information stored in the reagent information database 36 of the hard disc 401d is read by the controller 4a in step S111.

As shown in FIG. 31, in step S112, whether or not information indicating which icon of each icon (no additional information icon 428a, elapsed time icon 428b, reagent remaining amount icon 428c and remaining number of tests icon 428d) of the selection accepting region 428 of the reagent management screen 410 is selected is stored in the hard disc 401d is determined in time of display of the previous reagent management screen 410 by the controller 4a. If the information indicating which icon of the selection accepting region 428 is selected is stored in the hard disc 401d, the process proceeds to step S113 and the reagent management screen 410 reflecting the selected content (selection of icon) is displayed on the display 4b. In other words, the reagent information corresponding to the icon stored in the hard disc 401d is displayed on the additional information displaying portion (421c, 422c, and 423c) of each reagent mark (first reagent mark 421, second reagent mark 422, and diluting/cleaning fluid mark 423). Thus, when starting up the sample analyzer 1 and displaying the reagent management screen for the first time, the reagent information same as the reagent information displayed in each additional information displaying portion of the reagent management screen 410 before the sample analyzer 1 is shut down at the previous time is displayed. Thereafter, the process is returned. If the information indicating which icon of the selection accepting region 428 is selected is not stored in the hard disc 401d in step S112, the process proceeds to step S114. In step S114, the reagent management screen 410 in which the reagent information is not displayed and only the "reagent name" is displayed in each reagent mark is displayed in each additional information displaying portion by the controller 4a. Thereafter, the process is returned.

Figure 28:
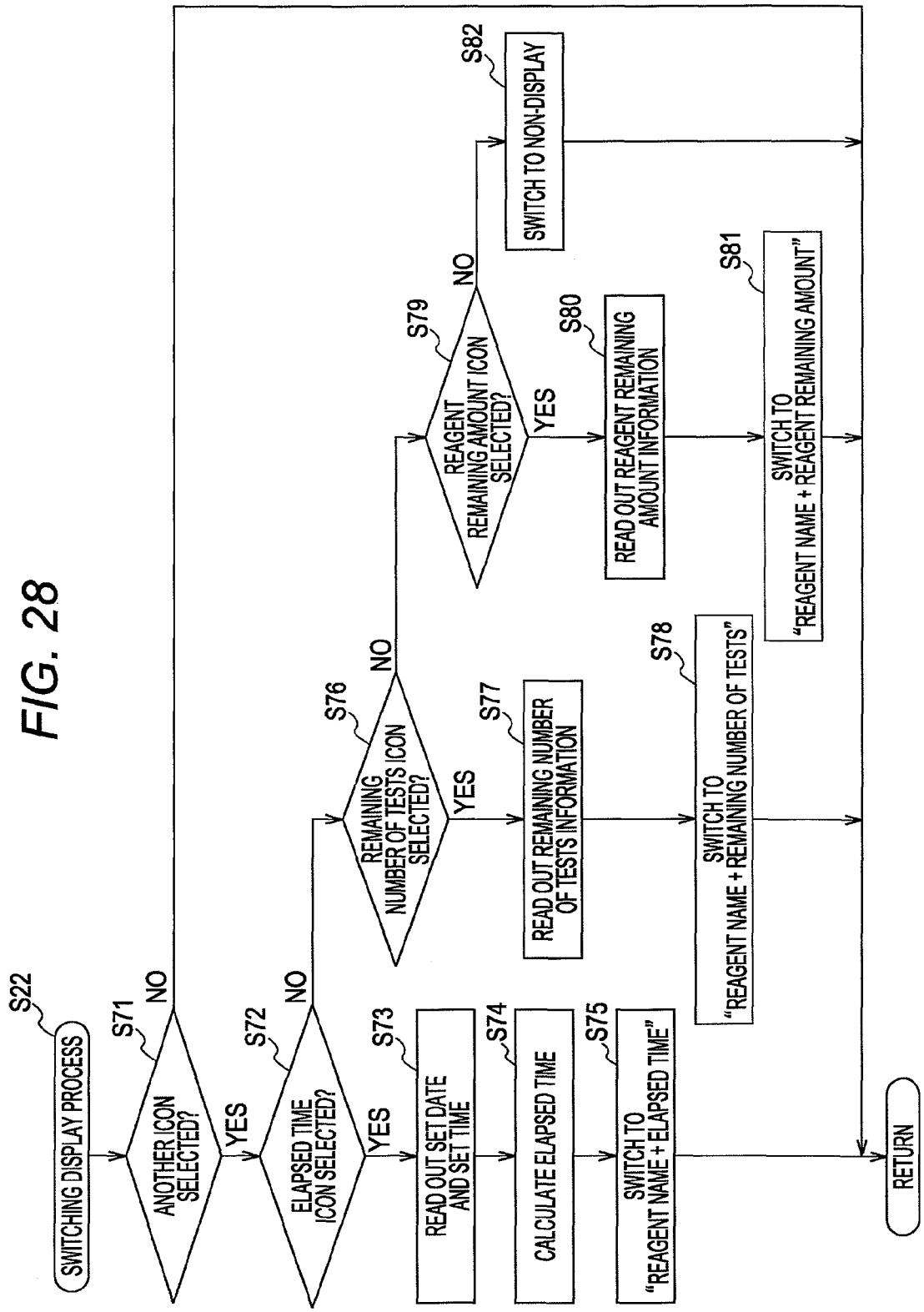
FIG. 28 is a flowchart for describing the switching display process in the reagent management screen of the sample analyzer according to one embodiment of the present invention.

FIG. 28 is a flowchart for describing details of the switching display process in the reagent management screen of the control device executed in step S22 of the flowchart shown in FIG. 22. The switching display process flow in the reagent management screen 410 will be described with reference to FIGS. 7 to 15 and 28. The switching display process is a process of switching displaying the reagent information displayed in the respective additional information displaying portion 421c, 422c, and 423c of the first reagent mark 421, the second reagent mark 422, and the diluting/cleaning fluid mark 423 in the reagent management screen 410 according to the selection of each icon in the selection accepting region 428 from the user.

First, in step S71, whether or not another icon different from the icon currently selected in the selection accepting region 428 of the reagent management screen 410 is selected is determined by the controller 4a, wherein the process proceeds to step S72 if another icon is selected and the process returns if another icon is not selected. In step S72, whether or not the icon selected in step S71 is the elapsed time icon 428b is determined by the controller 4a. If the icon selected in step S71 is the elapsed time icon 428b, the process proceeds to step S73. If the icon selected in step S71 is not the elapsed time icon 428b, the process proceeds to step S76.

In step S73, the record in which the data related to the set date and the set time is stored in each field of "set date" and "set time" of all the records of the reagent information database 36 of the hard disc 401d is searched by the controller 4a, and the data stored in each field of the "set date" and the "set time" of such record are read out by the controller 4a. In step S74, the elapsed time from being set to the reagent storing part 6 is calculated by the controller 4a for each reagent arranged in the reagent storing part 6 by subtracting the set date and set time read in step S73 from the current date and time. Thereafter, as shown in FIGS. 9 and 10, the process proceeds to step S75, the display of each reagent mark in the reagent arrangement displaying region 420 is switched to "reagent name+ elapsed time". The elapsed time is not displayed for the reagent mark corresponding to the record in which the data of the "set date" and "set time" are not read out in step S72. The process returns after the elapsed time information of the reagent is displayed in each reagent mark (first reagent mark 421, second reagent mark 422, and diluting/cleaning fluid mark 423) in the reagent arrangement displaying region 420.

If determined that the icon selected in step S71 is not the elapsed time icon 428b by the controller 4a in step S72, whether or not the icon selected in step S71 is the remaining number of tests 428d is determined by the controller 4a in step S76. If the icon selected in step S71 is the remaining number of tests icon 428d, the process proceeds to step S77. If the icon selected in step S71 is not the remaining number of tests icon 428d, the process proceeds to step S79.

In step S77, the record in which the data related to the remaining number of tests is stored in the field of "remaining number of tests" of all the records of the reagent information database 36 of the hard disc 401d is searched, and the data stored in the field of "remaining number of tests" of the record is read by the controller 4a. When the data of the field "remaining number of tests" is read out from the reagent information database 36 of the hard disc 401d, the process proceeds to step S78, and the display of each reagent mark in the reagent arrangement displaying region 420 is switched to "reagent name+remaining number of tests", as shown in FIGS. 13 and 14. The remaining number of tests is not displayed for the reagent which remaining amount is unknown (see FIG. 15) in which "remaining number of tests" is not calculated, and the reagent mark displayed with the error arrangement mark B, the expired mark C and the barcode reading error mark E in each reagent mark. The process returns after the remaining number of tests information of the reagent is displayed in each reagent mark (first reagent mark 421, second reagent mark 422, and diluting/cleaning fluid mark 423) in the reagent arrangement displaying region 420.

If determined that the icon selected in step S71 is not the remaining number of tests icon 428d by the controller 4a in step S76, whether or not the icon selected in step S71 is the reagent remaining amount 428c is determined by the controller 4a in step S79. If the icon selected in step S71 is the reagent remaining amount icon 428c, the process proceeds to step S80. If the icon selected in step S71 is not the reagent remaining amount icon 428c, the process proceeds to step S82.

In step S80, the record in which the data related to the usable amount is stored in the field of "usable amount (reagent remaining amount)" of all the records of the reagent information database 36 of the hard disc 401d is searched, and the data stored in the field of the "usable amount" of such record is read out by the controller 4a. When the data of the field "usable amount (reagent remaining amount)" is read out from the reagent information database 36 of the hard disc 401d, the process proceeds to step S81, and the display of each reagent mark in the reagent arrangement displaying region 420 is switched to "reagent name+reagent remaining amount (usable amount)", as shown in FIGS. 11 and 12. The usable amount is not displayed for the reagent which remaining amount is unknown (see FIG. 15) in which "usable amount" is not calculated, and the reagent mark displayed with the error arrangement mark B, the expired mark C and the barcode reading error mark E in each reagent mark. The process returns after the reagent remaining amount information is displayed in each reagent mark (first reagent mark 421, second reagent mark 422, and diluting/cleaning fluid mark 423) in the reagent arrangement displaying region 420.

If determined that the icon selected in step S71 is not the reagent remaining amount icon 428c in step S79, the icon selected in step S71 is determined as the no additional information icon 428a, and the display of each reagent mark in the reagent arrangement displaying region 420 is switched to only "reagent name" (non-display of reagent information other than reagent name), as shown in FIGS. 7 and 8, by the controller 4a in step S82. Thereafter, the process returns.

The switching display process in the reagent management screen 410 is performed by the controller 4a in such manner. The selection accepting process of each icon and the display switching process of each reagent mark in the selection accepting region 428 shown after step S71 are executed by so-called event-driven in which the process is performed in correspondence to the operation (event) executed by the user. Thus, the selection of each icon is always accepted, and the display switching of each reagent mark is performed during the display of the reagent management screen 410.

Figure 29:
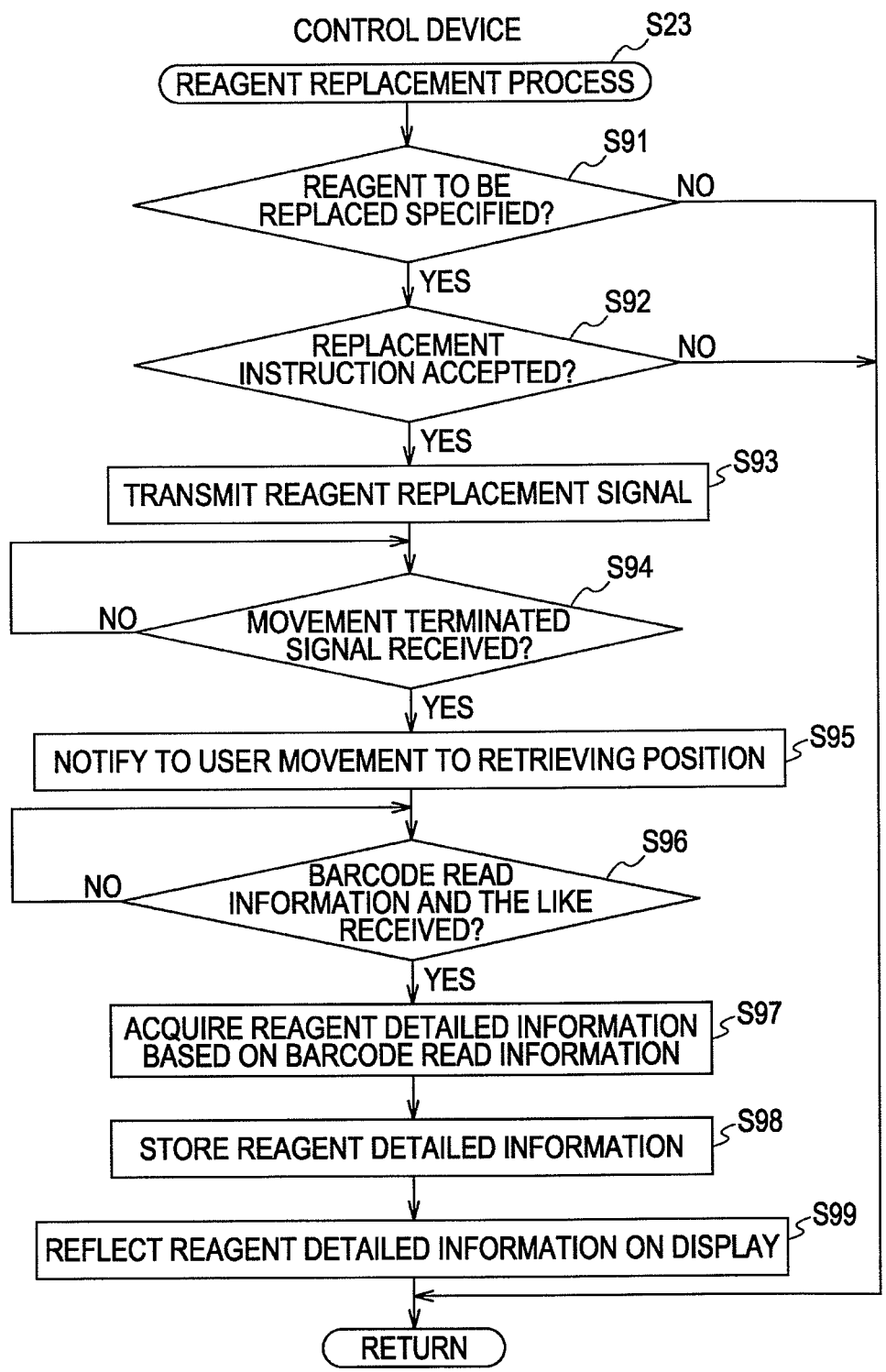
FIG. 29 is a flowchart for describing a reagent replacement process by the control device of the sample analyzer according to one embodiment of the present invention.
Figure 30:
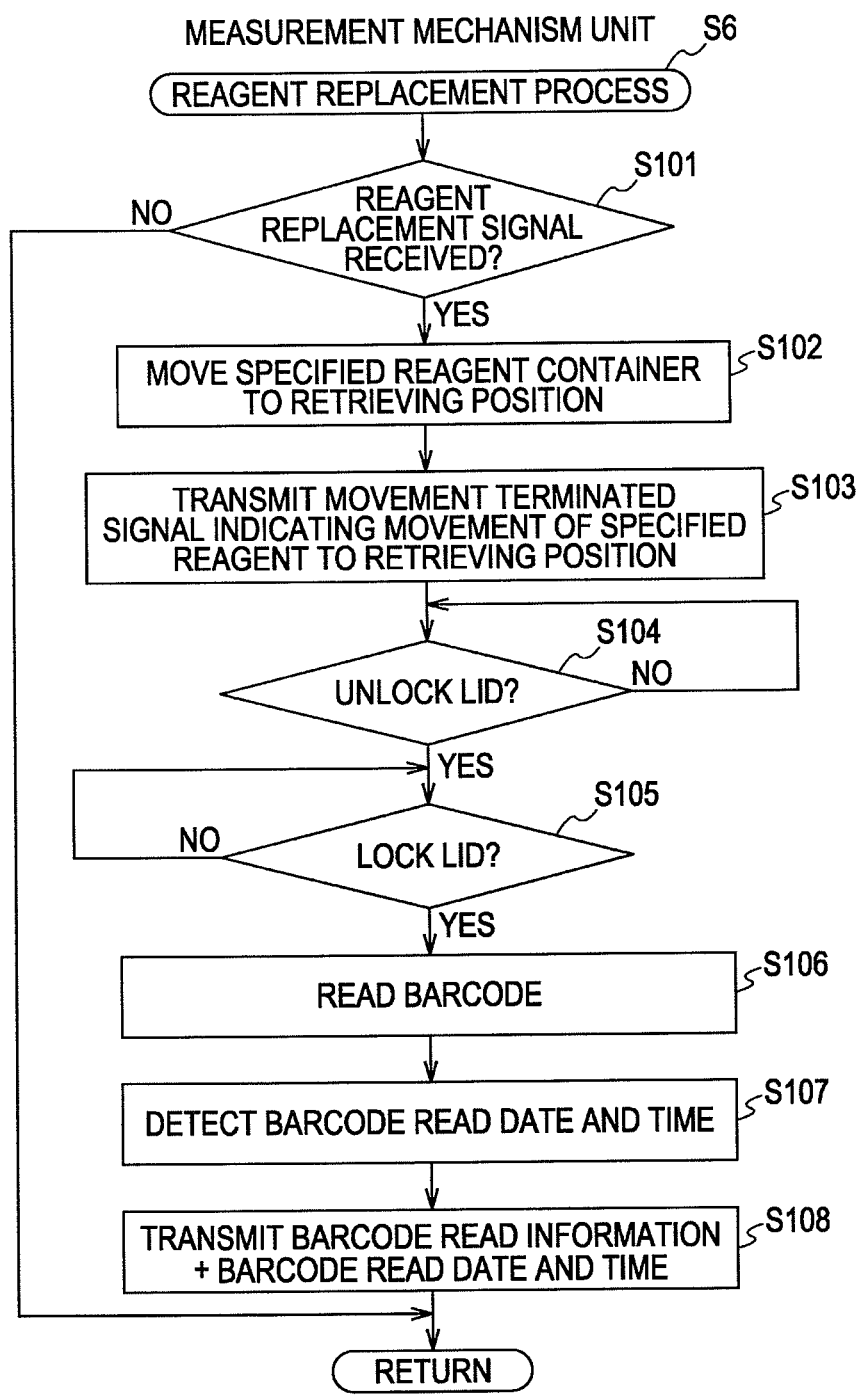
FIG. 30 is a flowchart for describing the reagent replacement process by the measurement mechanism unit of the sample analyzer according to one embodiment of the present invention.

FIG. 29 is a flowchart for describing the details of the reagent replacement process of the control device executed in step S23 of the flowchart shown in FIG. 22. FIG. 30 is a flowchart for describing the details of the reagent replacement process of the measurement mechanism unit executed in step S7 of the flowchart shown in FIG. 22. The reagent replacement process flow of the control device 4 and the measurement mechanism unit 2 of the sample analyzer 1 according to the present embodiment will be described below with reference to FIGS. 5, 7, 29, and 30.

As shown in FIG. 29, whether or not the reagent mark of the reagent to be replaced is specified is first determined by the controller 4a of the control device 4 in step S91. If the reagent is not specified, the process is returned. If the reagent is specified, whether or not the replacement instruction is accepted is determined by determining whether or not the replacement/addition instructing button 440a is pushed in step S92. If the instruction to replace the reagent is accepted, the process proceeds to step S93. If the instruction to replace the reagent is not accepted, the process is returned. In step S93, the controller 4a of the control device 4 transmits the reagent replacement signal to the controller 501 of the measurement mechanism unit 2.

The controller 501 of the measurement mechanism unit 2 determines whether or not the reagent replacement signal is received in step S101 of FIG. 30. If the reagent replacement signal is not received, the reagent replacement process of the measurement mechanism unit 2 is terminated.

If the reagent replacement signal is received, the first driving part 502 or the second driving part 503 is controlled by the controller 501 to rotate the reagent table of the reagent replacement target so that the first reagent container rack 310 or the second reagent container rack 320 holding the specified reagent is moved to the retrieving position (lower side of first lid 30 or second lid 40) in step S102. In this process, the controller 501 issues a command to instruct the movement with respect to the drive circuit of the reagent replacement target table. When the drive circuit accepts such command, the reagent replacement flag of the status register incorporated in the drive circuit is set. That is, the reagent replacement status is set to ON with respect to the reagent replacement target table including the reagent replacement instructed by the user. Either one of the reagent replacement status of the first reagent table 11 or the reagent replacement status of the second reagent table 12 is set to ON. When the reagent container rack holding the specified reagent is moved to the retrieving position, the movement terminated signal indicating that the reagent container rack holding the specified reagent is moved to the retrieving position is transmitted to the controller 4a of the control device 4 by the controller 501 in step S103. The controller 501 can determine the rotation movement amount of each reagent table 11, 12 from the origin position of the first reagent table 11 and het second reagent table 12 by counting the number of pulses of the drive pulse signal provided to the first driving part 502 or the second driving part 503. Thus, the controller 501 can recognize that the first reagent table 11 or the second reagent table 12 has moved to the retrieving position by the movement amount from the origin position, and can generate the movement terminated signal based on such recognition.

When the movement terminated signal is transmitted from the controller 501 to the controller 4a, whether or not the movement terminated signal is received is determined by the controller 4a in step S94 shown in FIG. 29. If determined that the movement terminated signal is received in step S94, the user is notified that the reagent container rack holding the specified reagent has been moved to the retrieving position in step S95. Specifically, the rack mark displayed in a predetermined color (e.g., yellow) is displayed in a different color (e.g., green) in the reagent management screen 410. In the reagent replacing part 7, when the reagent container rack holding the specified reagent is moved to the retrieving position, the LED indicator 51 or the LED indicator 52 that emits light in red during the movement of the reagent container rack emits light in blue. The user is thereby notified that the reagent container rack holding the specified reagent has been moved to the retrieving position.

For the replacement task of the reagent, the lock mechanism of the lid (first lid 30 or second lid 40) of the table of the reagent replacement target (first reagent table 11 or second reagent table 12) is released by the user. An unlock signal is transmitted to the controller 501 from a lock detector of the lid, and whether or not the lock of the lid is released is determined by the controller 501 in step S104. In the reagent replacement task by the user, the first lid 30 or the second lid 40, which lock state is released, is detached by the user, and thereafter, the grip (grip 313 or 327) of the reagent container rack at the retrieving position (lower side of first lid 30 or second lid 40) is gripped and taken out by the user. The reagent container 300 accommodating the specified reagent is then replaced with the reagent container 300 accommodating the new reagent by the user. Thereafter, the reagent container rack arranged with the reagent after the replacement is returned to the retrieving position, and the first lid 30 or the second lid 40 is attached and locked by the user. The lock signal is transmitted to the controller 501 from the lock detector of the lid, and whether or not the lid is locked is determined by the controller 501 in step S105.

If determined that the first lid 30 or the second lid 40 is locked by the controller 501 in step S105, the barcode reading operation is performed in step S106. In the barcode reading operation, the controller 501 controls the first reagent table 11 or the second reagent table 12 and the reagent barcode reader 350 so that the reagent barcode reader 350 reads the barcode with respect to the first reagent container rack 310 or the second reagent container rack 320 arranged with the replaced reagent. Specifically, when reading the barcodes 300a, 321b to 326b or 321c to 326c of the second reagent container rack 320 and the reagent container 300 held in the second reagent container rack 320, the barcode 321b for identifying the positional information (holder number) is first read while rotating the second reagent table 12 in the direction of the arrow G (counterclockwise direction) of FIG. 5. Subsequently, the barcode 300a for identifying the detailed identification information or the barcode 321c for identifying the no-container information is read, and then the barcode 322b representing the positional information is read. The positional information (holder number) (barcodes 321b to 326b) and the detailed identification information (barcode 300a) or the no-container information (barcodes 321c to 326c) corresponding to the positional information are alternately read. The detailed identification information includes the container kind information, the reagent ID, and the lot number.

When reading the barcodes 300a, 311b to 312b, or 311c to 312c of the first reagent container rack 310 and the reagent container 300 held in the first reagent container rack 310, the second reagent table 12 is first rotatably moved so that the gap 12a (see FIG. 5) of the second reagent table 12 reaches the position facing the reagent barcode reader 350. Thereafter, similar to the case of reading the barcode 300a of the second reagent container rack 320 and the reagent container 300 held in the second reagent container rack 320, the reagent barcode reader 350 alternately reads the positional information (holder number) (barcodes 311b to 312b) and the detailed identification information (barcode 300a) or the no-container information (barcodes 311c to 312c) corresponding to the positional information through the gap 12a (see FIG. 5) while rotating the first reagent table 11 in the direction of the arrow G (counterclockwise direction). The read positional information and the detailed identification information or the no-container information corresponding to the positional information (holder number) are transmitted to the controller 501 and stored in the RAM 501c. The barcode read date and time are detected in step S107.

In step S108, the barcode read information and the barcode read date and time stored in the RAM 501c are transmitted to the controller 4a by the controller 501.

When the barcode read information and the barcode read date and time are transmitted from the controller 501 to the controller 4a, whether or not the barcode read information and the barcode read date and time are received is determined by the controller 4a in step S96 shown in FIG. 29. If determined that the barcode read information and the barcode read date and time are received in step S96, the reagent detailed information including the set date and the set time of the reagent is acquired based on the barcode read information and the barcode read date and time in step S97. Specifically, the detailed information such as the reagent name, the kind of container, the lot number, and the expiration date are acquired for all the reagents in the reagent rack holding the replaced reagent with reference to the reagent master, the reagent lot master, and the container master based on the barcode read information ((positional information), the holder number, the reagent ID, the container kind information, and the like). More specifically, the "holder number" is specified from the positional information of the barcode of the reagent container rack. The reagent ID and the reagent setting information are matched, and the "reagent name" and the "presence of stirring" are specified. Furthermore, the reagent lot number and the reagent lot setting information are matched, and the "reagent lot number" and the "expiration date" are specified. The container ID and the container selling information are matched, and the "container kind" is specified. Since the remaining amount of the reagent is calculated as described above for the reagent used in the measurement, the "usable amount" and the "remaining number of tests" are specified from the calculated remaining amount of the reagent. If the reagent is not used for the measurement not even once after the replacement, the "usable amount" and the "remaining number of tests" are not calculated. The "set date" and the "set time" for the replaced reagent are specified by the date and time where the barcode is read, and the "set date" and the "set time" for the non-replaced reagent are not specified.

In step S98, the reagent detailed information including the set date and the set time of the reagent are stored in the reagent information database 36 of the hard disc 401d. In this case, the reagent detailed information of the reagent retrieved from the reagent storing part 6 by replacement is deleted from the reagent information database 36, and the reagent detailed information of the reagent newly set in the reagent storing part 6 by replacement is newly stored in the reagent information database 36. The reagent detailed information on the non-replaced reagent is remained saved in the reagent information database 36. Since the "usable amount" and the "remaining number of tests" of the replaced reagent are unknown, "- (hyphen)" is stored in the field of "usable amount" and "remaining number of tests" of the reagent information database 36 with respect to the reagent newly set in the reagent storing part 6 by replacement. In step S99, the reagent detailed information such as the positional information, the reagent name, the kind of container, the lot number, the expiration date, the usable amount, and the remaining number of tests are reflected by the controller 4a on the first reagent mark 421, the second reagent mark 422 or the no-reagent arrangement mark 427 and the reagent detailed displaying region 430 of the reagent management screen 410 (see FIG. 7). In this case, since the remaining amount of the replaced reagent is unknown, the remaining amount indicator is displayed with a predetermined color (gray).

In the present embodiment, one of the three kinds of reagent information (elapsed time information, reagent remaining amount information, and remaining number of tests information) related to each reagent placed in the first reagent table 11, the second reagent table 12, and the holder 141 is displayed in each reagent mark (first reagent mark 421, second reagent mark 422, and diluting/cleaning fluid mark 423). Since the reagent information can be displayed on each of the plurality of reagent marks, the user can easily grasp at one sight the reagent information of a plurality of reagents placed in the first reagent table 11, the second reagent table 12, and the holder 141. When accepting the selection of each icon (no-additional information icon 428a, elapsed time icon 428b, reagent remaining amount icon 428c, and remaining number of tests icon 428d) of the selection accepting region 428, the reagent information displayed on each of the plurality of reagent marks is switched to the reagent information corresponding to the selected icon. Thus, the reagent information displayed on each of the plurality of reagent marks can be selectively displayed from the three kinds of reagent information. Thus, excess information is suppressed, and the user can easily grasp the necessary reagent information.

In the present embodiment, if the selection of another icon is accepted when one of the reagent information is displayed on each of the plurality of reagent marks (first reagent mark 421, second reagent mark 422, and diluting/cleaning fluid 423), the reagent information displayed on each of the plurality of reagent marks is switched to the selected another kind of reagent information. The user can thus easily switch the reagent information displayed on the plurality of reagent marks to the necessary reagent information by simply selecting from the plurality kinds of reagent information.

In the present embodiment, the controller 4a is configured so as to accept the selection of the reagent information corresponding to the selected icon when a predetermined icon of the selection accepting region 428 is selected. Thus, the reagent information displayed on each of the plurality of reagent marks (first reagent mark 421, second reagent mark 422, and diluting/cleaning fluid mark 423) can be selected by simply selecting a plurality of icons of the selection accepting region 428 contained in the reagent management screen 410. Thus, the user can perform the selection of the necessary reagent information (pushing of icon) and the display to the additional information displaying portion (421c, 422c, and 423c) in the same reagent management screen 410.

In the present embodiment, the background color of the selected icon of the plurality of icons in the selection accepting region 428 is changed to orange. Thus, from the selection of which icon of the plurality of icons the reagent information displayed on a plurality of reagent marks (first reagent mark 421, second reagent mark 422, and diluting/cleaning fluid mark 423) is displayed can be identified. The user thus can easily grasp which reagent information of the plurality kinds of reagent information the reagent information displayed on each reagent mark is.

In the present embodiment, the no-additional information icon 428a is arranged in the selection accepting region 428. Thus, the user can switch the reagent information in the additional information displaying portion (421c, 422c, and 423c) of each reagent mark to non-display, as necessary, by selecting the no-additional information icon 428a from the selection accepting region 428 displayed on the display screen.

In the present embodiment, the selection of the reagent information to display is accepted by icon. The user can intuitively recognize and select the plurality kinds of reagent information by the respective icon.

In the present embodiment, the reagent arrangement displaying region 420 including a schematic view of the annular first reagent table 11, the second reagent table 12 and the holder 141 is arranged on the reagent management screen 410 so as to surround the selection accepting region 428. The user can intuitively grasp the arrangement of the reagent of the first reagent table 11, the second reagent table 12, and the holder 141 by simply looking at the reagent arrangement displaying region 420 displayed in an annular form, and can effectively use the display space since the selection accepting region 428 can be arranged in a portion where the reagent mark is not arranged at the middle of the annular reagent arrangement displaying region 420.

In the present embodiment, a plurality of reagent marks (first reagent mark 421, second reagent mark 422, and diluting/cleaning fluid 423) schematically showing the reagent are displayed on the reagent arrangement displaying region 420, and one of the reagent information is displayed on the additional information displaying portion (421c, 422c, and 423c) in the plurality of reagent marks. Thus, the arrangement of each reagent mark of the reagent arrangement displaying region 420 of the reagent management screen 410 is displayed in correspondence to the actual arrangement of the reagent in the first reagent table 11, the second reagent table 12 and the holder 141 and the reagent information is displayed in each reagent mark, whereby the user can check the reagent information in correspondence with the arrangement position of the reagent by looking at the display of the reagent mark.

In the present embodiment, the controller 4a displays the reagent detailed information including the reagent information displayed in the additional information displaying portion of each reagent mark in the detailed information displaying region 430. The user thus grasps the reagent information (elapsed time information, reagent remaining amount information, and remaining number of tests information) displayed in a plurality of reagent marks with the arrangement state of the reagent, and then specifies the reagent mark requiring check, and displays the reagent detailed information in the detailed information displaying region 430. Thus, the user can easily grasp both the overall state of the reagent placed in great numbers in the first reagent table 11, the second reagent table 12, and the holder 141 and the detailed information of the reagent requiring check, and the workability can be enhanced.

In the present embodiment, the selection accepting region 428 includes the elapsed time icon 428b for selecting the elapsed time information, the reagent remaining amount icon 428c for selecting the reagent remaining amount information, the remaining number of tests icon 428d for selecting the remaining number of tests information, and the no-additional information icon 428a for having the display of the reagent information in each of the plurality of reagent marks to non-display. Thus the user can selectively display all at once the reagent remaining amount information that requires frequent check for reagent replacement, the remaining number of tests information of the reagent for grasping the measureable number of times, and the elapsed time information for determining the expiration date of each region to each of the additional information displaying portion of a plurality of reagent marks by selecting the reagent remaining amount icon 428c, the remaining number of tests icon 428d, and the elapsed time icon 428b in terms of using the sample analyzer 1. Thus, the information necessary to be frequently checked can be listed, as necessary, and grasped.

In the present embodiment, the kind of reagent information displayed in the additional information displaying portion (421c, 422c, and 423c) of each reagent mark in time of display of the reagent management screen 410 of the previous time is stored in the hard disc 401d, and the reagent information of the kind stored in the hard disc 401d is displayed in the additional information displaying portion of each reagent mark in time of display of the reagent management screen 410 of the next time. Thus, the reagent information same as the reagent information selected in the reagent management screen 410 of the previous time does not need to be displayed in each reagent mark by selecting the icon every time the sample analyzer 1 is started (reagent management screen is displayed), whereby the reagent information can be checked without performing extra switching task. Since only specific reagent information can be constantly displayed in the reagent mark, the reagent information constantly required by the user can be constantly displayed.

In the present embodiment, the controller 4a displays the plurality of reagent information displayed in the reagent name displaying portion and the additional information displaying portion of the plurality of reagent marks on the remaining amount indicator (421d, 422d, and 423d) in an overlapping manner. Since the remaining amount information can be displayed as a background on the information displayed in each reagent mark in an overlapping manner, the plurality of reagent information (reagent name, reagent information of additional information displaying portion, and remaining amount information) can be displayed without enlarging each reagent mark. Thus, greater amount of reagent information can be displayed on the reagent management screen 410 without enlarging the displaying region.

In the present embodiment, the remaining amount indicator (421d, 422d, and 423d) displays the information related to the remaining amount of each reagent placed in the first reagent table 11, the second reagent table 12, and the holder 141. Thus, in terms of using the sample analyzer 1, the information related to the remaining amount of the reagent that requires frequent check for reagent replacement can be constantly displayed as a background on the display of the reagent information displayed in each reagent mark in an overlapping manner.

The embodiments disclosed herein should be construed as illustrative and not restrictive in all aspects. The scope of the invention is defined by the claims rather than by the description of the embodiments, and includes all modifications equivalent in meaning to the claims and within the scope of the claims.

For instance, in the embodiment described above, an example in which one reagent information is selectively displayed in the additional information displaying portion by selecting one of the icons of the selection accepting region has been described, but the present invention is not limited thereto. Plural reagent information may be displayed in the additional information displaying portion by selecting plural icons.

In the embodiment described above, an example in which the elapsed time information, the reagent remaining amount information, and the remaining number of tests information are selectively displayed in a switchable manner in the additional information displaying portion of each reagent mark has been described, but the present invention is not limited thereto. Information other than the elapsed time information, the reagent remaining amount information, and the remaining number of tests information such as presence of stirring and expiration date of the reagent may be selectively displayed in a switchable manner in the additional information displaying portion of each reagent mark. The kind of reagent information displayable in the additional information displaying portion may be set by the user.

In the embodiment described above, an example in which the reagent information is displayed in the additional information displaying portion of all the reagent marks (first reagent mark 421, second reagent mark 422, and diluting/cleaning fluid mark 423) of the reagent arrangement displaying region 420 by selecting one of the icons of the selection accepting region has been described above, but the present invention is not limited thereto. The reagent information may be displayed at one part of each reagent mark arranged in the reagent arrangement displaying region 420. For instance, the reagent information may be displayed in the additional information displaying portion of only either the first reagent mark or the second reagent mark.

In the embodiment described above, an example in which the icon of the selection accepting region is selectably displayed has been described, but the present invention is not limited thereto. In addition to the icons, characters and the like may be simultaneously described or selecting portions (buttons) other than icons may be provided. For instance, a button including only the character displaying the reagent information displayed in the additional information displaying portion may be provided.

In the embodiment described above, an example in which the selection accepting region 428 is arranged to be surrounded by the annular reagent arrangement displaying region 420 has been described, but the present invention is not limited thereto. The selection accepting region may not be arranged to be surrounded by the reagent arrangement displaying region. The selection accepting region may be configured such that each item name ("usable amount", "remaining number of tests", and the like) of the reagent detailed information displayed in the reagent detailed information displaying region 430 is selectable as the selection accepting region, so that the reagent information displayed in the additional information displaying portion of each reagent mark can be switched by selecting the item name.

In the embodiment described above, an example in which four icons (no-additional information icon 428a, elapsed time icon 428b, reagent remaining amount icon 428c, and remaining number of tests icon 428d) are selectably arranged in the selection accepting region has been described, but the present invention is not limited thereto. Two, three, or five or more icons may be selectably arranged in the selection accepting region.

In the embodiment described above, an example in which the reagent information displayed in the additional information displaying portion of each reagent mark is selectable by selecting each icon of the selection accepting region has been described above, but the present invention is not limited thereto. The switching of the reagent information displayed in each reagent mark may be such that the remaining number of tests, the reagent remaining amount, the elapsed time, and the no-additional information are switched in order by double clicking the reagent management screen. A "switch display" icon may be provided, so that switch is made in order by clicking such icon. When arranging such "switch display" icon, the information indicating the reagent information displayed in the additional information displaying portion of each reagent mark may be displayed in a predetermined region of the "switch display" icon, and the information in the predetermined region of the "switch display" icon may be switched according to the clicking of the user. For instance, if the reagent remaining number of tests is displayed in the additional information displaying portion of each reagent mark, "remaining number of tests" is displayed in a predetermined region of the "switch display" icon, wherein "elapsed time" is displayed in the predetermined region in the "switch display" icon when the reagent information of the additional information displaying portion of each reagent mark is switched to the elapsed time information according to the clicking of the user.

In the embodiment described above, an example in which the reagent information displayed in the additional information displaying portion of each reagent mark is set to non-display by selecting (pushing) the no-additional information icon 428a of the selection accepting region has been described above, but the present invention is not limited thereto. For instance, the reagent information may be displayed in each reagent mark when each icon is selected (pushed) once, and the reagent information displayed in each reagent mark may be non-displayed when the same icon is again selected (pushed).

In the embodiment described above, an example in which the reagent information displayed in the additional information displaying portion of each reagent mark is switched by selecting the icon of the selection accepting region has been described, but the present invention is not limited thereto. For instance, when the sample analyzer detects lack of reagent remaining amount or that the elapsed time has exceeded the tolerable range, an alarm indicating that the remaining amount of reagent is lacking or that the elapsed time is abnormal may be displayed on the display screen. The reagent information displayed in the additional information displaying portion of each reagent mark may be automatically switched to the reagent remaining amount information if the remaining amount of reagent is lacking, and the reagent information displayed in the additional information displaying portion of each reagent mark may be automatically switched to the elapsed time information if the elapsed time is abnormal. Furthermore, a dialog for indicating that the remaining amount of reagent is lacking or that the elapsed time is abnormal and for accepting whether or not to switch the reagent information displayed in the additional information displaying portion of each reagent mark may be displayed on the display screen, wherein the reagent information displayed in the additional information displaying portion of each reagent mark may be switched to the reagent remaining amount information or the elapsed time information when accepting the switch instruction of the reagent information from the user at the relevant dialog.

In the embodiment described above, an example in which the remaining amount of reagent corresponding to each reagent mark is background displayed by the remaining amount indicator has been described, but the present invention is not limited thereto. For instance, the expiration date of the reagent may be background displayed by the indicator.

In the embodiment described above, an example in which the remaining amount of reagent is displayed in light blue by the remaining amount indicator, displayed in yellow when reaching the number of warning tests, and warning displayed in red when reaching the number of interrupted tests has been described, but the present invention is not limited thereto. The display of the remaining amount indicator may be displayed by combining colors different from the above example.

In the embodiment described above, an example in which the remaining amount indicator is displayed such that the light blue region reduces with reduction of the reagent remaining amount in the reagent container 300 in the reagent mark has been described, but the present invention is not limited thereto. The display of the remaining amount indicator may be only change in color. In other words, without reducing the light blue region according to reduction of the remaining amount, the background of the reagent mark may be displayed in light blue when the remaining number of tests is greater than the number of warning tests, the background may be displayed in yellow when reaching the number of warning tests, and the background may be displayed in red when reaching the number of interrupted tests.

In the embodiment described above, an example in which the display has a touch panel function and is selectable or operable by having the user directly touch the button and the like displayed on the reagent management screen has been described, but the present invention is not limited thereto. The display may be selectable or operable by specifying the button and the like displayed on the reagent management screen by a keyboard or a mouse.

What is claimed is:

1. A sample analyzer, comprising:
a reagent holder for holding a first reagent and a second reagent used for analysis of a sample;
an analyzing unit configured to analyze the sample by using at least one of the first reagent and the second reagent:
a display;
a display controller programmed to display a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information; and a display switch receiver for receiving a display switch instruction of reagent information displayed in each of the first and second information displaying regions, wherein the display controller switches the first reagent information displayed in the first information displaying region to the second reagent information and switches the third reagent information displayed in the second information displaying region to the fourth reagent information, when the display switch receiver has received the display switch instruction, wherein the display controller is programmed to display an information of expiration of the first reagent and not to display the first reagent information in the first information displaying region when the first reagent is expired, wherein the display controller is programmed to, when the information of expiration of the first reagent is displayed in the first information displaying region and the third reagent information is displayed in the second information displaying region, keep displaying the information of expiration of the first reagent in the first information displaying region and switch the third reagent information in the second information displaying region to the fourth reagent information in response to receiving the display switch instruction by the display switch receiver, wherein the first and third reagent information is one of elapsed time information indicating an elapsed time since the first reagent was held by the reagent holder, reagent remaining amount information indicating remaining amount of the first reagent held by the reagent holder, and usable number of times information indicating usable number of times of the first reagent held by the reagent holder, wherein the second and fourth reagent information is one of elapsed time information indicating an elapsed time since the second reagent was held by the reagent holder, reagent remaining amount information indicating remaining amount of the second reagent held by the reagent holder, and usable number of times information indicating usable number of times of the second reagent held by the reagent holder, the second and fourth reagent information being different from the first and third reagent information.

2. The sample analyzer of claim 1, wherein a first display selecting portion for selecting display of the first and third reagent information in the first and second information displaying regions respectively and a second display selecting portion for selecting display of the second and fourth reagent information in the first and second information displaying regions respectively are displayed on the display screen as the display switch receiver.

3. The sample analyzer of claim 2, wherein the plurality of reagent information regarding the first reagent comprises a fifth reagent information, and the plurality of reagent information regarding the second reagent comprises a sixth reagent information, a type of the fifth reagent information being same as a type of the sixth reagent information; and wherein a third display selecting portion for selecting display of the fifth and sixth reagent information in the first and second information displaying regions respectively is displayed on the display screen as the display switch receiver.

4. The sample analyzer of claim 2, wherein a selected display selecting portion is displayed so as to be distinguishable from another non-selected display selecting portion.

5. The sample analyzer of claim 2, wherein the first display selecting portion comprises a first icon image showing the type of the first and third reagent information; and the second display selecting portion comprises a second icon image showing the type of the second and fourth reagent information.

6. The sample analyzer of claim 1, wherein a non-display selecting portion, for making reagent information displayed in each of the first and second information displaying regions disappear, is displayed on the display screen; and reagent information displayed in each of the first and second information displaying regions is disappeared when the non-display selecting portion has been selected.

7. The sample analyzer of claim 1, wherein a schematic diagram of the reagent holder is displayed on the display screen; and a first reagent information displaying portion which comprises the first information displaying region and a first name displaying region for displaying a name of the first reagent, and a second reagent information displaying portion which comprises the second information displaying region and a second name displaying region for displaying a name of the second reagent are displayed on the schematic diagram of the reagent holder according to positions of the first and second reagents in the reagent holder.

8. The sample analyzer of claim 7, wherein a detailed information displaying region for displaying detailed information including the plurality of reagent information of one of the first and second reagents held by the reagent holder is displayed on the display screen;

the first and second reagent information displaying portions are displayed so as to be selectable on the display screen; and the detailed information corresponding a selected reagent information displaying portion is displayed in the detailed information displaying region.

9. The sample analyzer of claim 7, wherein the first reagent information displaying portion further comprises a first background region at a background of the first information displaying region and the first name displaying region;

the second reagent information displaying portion further comprises a second background region at a background of the second information displaying region and the second name displaying region;

a change of remaining amount of the first reagent held by the reagent holder is displayed by a change in color of the first background region or a change in display area of a predetermined color of the first background region; and a change of remaining amount of the second reagent held by the reagent holder is displayed by a change in color of the second background region or a change in display area of a predetermined color of the second background region.

10. The sample analyzer of claim 2, wherein the reagent holder has an annular shape; and a schematic diagram of the annular reagent holder surrounding a selection receiving region including the first and second display selecting portions is displayed on the display screen.

11. The sample analyzer of claim 1, further comprising a memory for storing the plurality of reagent information regarding the first reagent and the plurality of reagent information regarding the second reagent, wherein the display controller reads out the second and fourth reagent information respectively from the memory, and switches the first reagent information displayed in the first information displaying region to the read-out second reagent information and switches the third reagent information displayed in the second information displaying region to the read-out fourth reagent information, when the display switch receiver has received the display switch instruction.

12. The sample analyzer of claim 1, further comprising a memory for storing reagent information displayed in each of the first and second information displaying regions when terminating a display of the display screen, wherein the display controller controls the display so as to display reagent information stored in the memory in each of the first and second information displaying regions when resuming the display of the display screen.

13. A sample analyzer, comprising:
   a reagent holder for holding a first reagent and a second reagent used for analysis of a sample;
   an analyzing unit configured to analyze the sample by using at least one of the first reagent and the second reagent;
   a display; and
   a control processing unit configured to perform operations comprising:
   controlling the display so as to display a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information;
   receiving a display switch instruction of reagent information displayed in each of the first and second information displaying regions; and
   switching the first reagent information displayed in the first information displaying region to the second reagent information, and switching the third reagent information displayed in the second information displaying region to the fourth reagent information, when received the display switch instruction,
   wherein the control processing unit is configured to control the display so as to display an information of expiration of the first reagent and not to display the first reagent information in the first information displaying region when the first reagent is expired,
   wherein the control processing unit is configured to control the display so as to, when the information of expiration of the first reagent is displayed in the first information displaying region and the third reagent information is displayed in the second information displaying region, keep displaying the information of expiration of the first reagent in the first information displaying region and switch the third reagent information in the second information displaying region to the fourth reagent information in response to receiving the display switch instruction by the display switch receiver,
   wherein the first and third reagent information is one of elapsed time information indicating an elapsed time since the first reagent was held by the reagent holder, reagent remaining amount information indicating remaining amount of the first reagent held by the reagent holder, and usable number of times information indicating usable number of times of the first reagent held by the reagent holder, and
   wherein the second and fourth reagent information is one of elapsed time information indicating an elapsed time since the second reagent was held by the reagent holder, reagent remaining amount information indicating remaining amount of the second reagent held by the reagent holder, and usable number of times information indicating usable number of times of the second reagent held by the reagent holder, the second and fourth reagent information being different from the first and third reagent information.

14. The sample analyzer of claim 13, wherein
   a first display selecting portion for selecting display of the first and third reagent information in the first and second information displaying regions respectively and a second display selecting portion for selecting display of the second and fourth reagent information in the first and second information displaying regions respectively are displayed on the display screen; and
   the control processing unit receives the display switch instruction to switch the first reagent information displayed in the first information displaying region to the second reagent information and to switch the third reagent information displayed in the second information displaying region to the fourth reagent information, when the second display selecting portion is selected in a state that the first and third reagent information is being displayed in the first and second information displaying regions respectively.

15. The sample analyzer of claim 14, wherein the first display selecting portion comprises a first icon image showing the type of the first and third reagent information; and
   the second display selecting portion comprises a second icon image showing the type of the second and fourth reagent information.

16. The sample analyzer of claim 13, wherein the plurality of reagent information regarding the first reagent include at least one of elapsed time information indicating an elapsed time since the first reagent was held by the reagent holder, reagent remaining amount information indicating remaining amount of the first reagent held by the reagent holder, and usable number of times information indicating usable number of times of the first reagent held by the reagent holder; and
   the plurality of reagent information regarding the second reagent include at least one of elapsed time information indicating an elapsed time since the second reagent was held by the reagent holder, reagent remaining amount information indicating remaining amount of the second reagent held by the reagent holder, and usable number of times information indicating usable number of times of the second reagent held by the reagent holder.

17. A reagent information displaying method in a sample analyzer including a reagent holder for holding a first reagent and a second reagent used for analysis of a sample, and a display, comprising:
   displaying, on the display, a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information;

receiving a display switch instruction of reagent information displayed in each of the first and second information displaying regions; and switching the first reagent information displayed in the first information displaying region to the second reagent information, and switching the third reagent information displayed in the second information displaying region to the fourth reagent information, when received the display switch instruction;

displaying the display screen including an information of expiration of the first reagent and not displaying the first reagent information in the first information displaying region when the first reagent is expired; and displaying the display screen so as to, when the information of expiration of the first reagent is displayed in the first information displaying region and the third reagent information is displayed in the second information displaying region, keep displaying the information of expiration of the first reagent in the first information displaying region and switch the third reagent information in the second information displaying region to the fourth reagent information in response to receiving the display switch instruction by the display switch receiver, wherein the first and third reagent information is one of elapsed time information indicating an elapsed time since the first reagent was held by the reagent holder, reagent remaining amount information indicating remaining amount of the first reagent held by the reagent holder, and usable number of times information indicating usable number of times of the first reagent held by the reagent holder, and wherein the second and fourth reagent information is one of elapsed time information indicating an elapsed time since the second reagent was held by the reagent holder, reagent remaining amount information indicating remaining amount of the second reagent held by the reagent holder, and usable number of times information indicating usable number of times of the second reagent held by the reagent holder, the second and fourth reagent information being different from the first and third reagent information.

18. The reagent information displaying method of claim 17, wherein the display screen includes a first display selecting portion for selecting display of the first and third reagent information in the first and second information displaying regions respectively and a second display selecting portion for selecting display of the second and fourth reagent information in the first and second information displaying regions respectively; and the display switch instruction to switch the first reagent information displayed in the first information displaying region to the second reagent information and to switch the third reagent information displayed in the second information displaying region to the fourth reagent information is received, when the second display selecting portion is selected in a state that the first and third reagent information is being displayed in the first and second information displaying regions respectively.

19. A non-transitory computer program product for enabling a computer to control a display device in a sample analyzer which comprises a reagent holder for holding a first reagent and a second reagent used for analysis of a sample, comprising:

a non-transitory computer readable medium, and software instruction, on the non-transitory computer readable medium, for enabling the computer to perform predetermined operations comprising:

controlling the display device so as to display a display screen including a first information displaying region for displaying one of a plurality of reagent information regarding the first reagent held by the reagent holder and a second information displaying region for displaying one of a plurality of reagent information regarding the second reagent held by the reagent holder, the plurality of reagent information regarding the first reagent comprising first and second reagent information, the plurality of reagent information regarding the second reagent comprising third and fourth reagent information, a type of the first reagent information being same as a type of the third reagent information, and a type of the second reagent information being same as a type of the fourth reagent information;

receiving a display switch instruction of reagent information displayed in each of the first and second information displaying regions; and switching the first reagent information displayed in the first information displaying region to the second reagent information, and switching the third reagent information displayed in the second information displaying region to the fourth reagent information, when received the display switch instruction, controlling the display device so as to display an information of expiration of the first reagent and not to display the first reagent information in the first information displaying region when the first reagent is expired, and controlling the display device so as to, when the information of expiration of the first reagent is displayed in the first information displaying region and the third reagent information is displayed in the second information displaying region, keep displaying the information of expiration of the first reagent in the first information displaying region and switch the third reagent information in the second information displaying region to the fourth reagent information in response to receiving the display switch instruction by the display switch receiver, wherein the first and third reagent information is one of elapsed time information indicating an elapsed time since the first reagent was held by the reagent holder, reagent remaining amount information indicating remaining amount of the first reagent held by the reagent holder, and usable number of times information indicating usable number of times of the first reagent held by the reagent holder, and wherein the second and fourth reagent information is one of elapsed time information indicating an elapsed time since the second reagent was held by the reagent holder, reagent remaining amount information indicating remaining amount of the second reagent held by the reagent holder, and usable number of times information indicating usable number of times of the second reagent held by the reagent holder, the second and fourth reagent information being different from the first and third reagent information.

\* \* \* \* \*